United States Patent
Song et al.

(10) Patent No.: US 10,709,612 B2
(45) Date of Patent: Jul. 14, 2020

(54) ODOR CONTROL ARTICLE

(71) Applicant: KIMBERLY-CLARK WORLDWIDE, INC., Neenah, WI (US)

(72) Inventors: Xuedong Song, Alpharetta, GA (US); Davis Dang H. Nhan, Appleton, WI (US); John Gavin MacDonald, Decatur, GA (US); Richard Arnold Borders, Marietta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 625 days.

(21) Appl. No.: 15/518,554

(22) PCT Filed: Jul. 28, 2015

(86) PCT No.: PCT/US2015/042358
§ 371 (c)(1),
(2) Date: Apr. 12, 2017

(87) PCT Pub. No.: WO2016/069072
PCT Pub. Date: May 6, 2016

(65) Prior Publication Data
US 2017/0274114 A1    Sep. 28, 2017

Related U.S. Application Data

(60) Provisional application No. 62/073,322, filed on Oct. 31, 2014.

(51) Int. Cl.
*A61L 15/46* (2006.01)
*A61F 13/00* (2006.01)
(Continued)

(52) U.S. Cl.
CPC .... *A61F 13/00063* (2013.01); *A61F 13/8405* (2013.01); *A61L 15/46* (2013.01); *A61F 2013/8408* (2013.01); *A61L 15/16* (2013.01)

(58) Field of Classification Search
CPC .... A61F 13/00063; A61L 15/16; A61L 15/20; A61L 15/425; A61L 15/46
See application file for complete search history.

(56) References Cited

U.S. PATENT DOCUMENTS 5,076,932 A * 12/1991 Taylor ............... B01D 61/00
                                                210/500.23
5,188,064 A *  2/1993 House ............... A01K 1/0154
                                                119/172
(Continued)

FOREIGN PATENT DOCUMENTS

CN    102112203 A    6/2011
CN    103249467 A    8/2013
(Continued)

OTHER PUBLICATIONS

Peter, M. Budd et al., "Gas Permeation Parameters and Other Physicochemical Properties of a Polymer of Intrinsic Microporosity: Polybenzodioxane PIM-1," Journal of Membrane Science, vol. 325, Issue 2, Dec. 1, 2008, pp. 851-860.
(Continued)

*Primary Examiner* — Susan S Su
(74) *Attorney, Agent, or Firm* — Kimberly-Clark Worldwide, Inc.

(57) ABSTRACT

Odor control articles (10) including hydrophobic polymers of intrinsic porosity (HPIM) and their use in personal care products and hygienic products is disclosed. The odor control article (10) includes a HPIM and a colorant. The odor control article (10) may be applied to a substrate (11), and more specifically to a liquid absorbent member (30), to form an odor-absorbing member (20). The substrate (11) may absorb liquid. The odor-absorbing member (20) may be placed in such products as diapers (200), incontinence pads (60) and refrigerator pads. A method of making an odor control suspension with HPIMs including the use of surfac-
(Continued)

tants is also disclosed. The odor control suspension may also be applied to a substrate (11).

15 Claims, 11 Drawing Sheets

(51) Int. Cl.
*A61L 15/16* (2006.01)
*A61F 13/84* (2006.01)

(56) References Cited

U.S. PATENT DOCUMENTS

| | | | |
|---|---|---|---|
| 6,147,028 A * | 11/2000 | Rizzi | A61F 13/8405 |
| | | | 502/404 |
| 6,433,243 B1 | 8/2002 | Woltman et al. | |
| 6,503,412 B1 | 1/2003 | Schroeder | |
| 7,132,479 B2 | 11/2006 | Engelhardt et al. | |
| 7,141,518 B2 | 11/2006 | MacDonald et al. | |
| 7,410,525 B1 | 8/2008 | Liu et al. | |
| 7,488,520 B2 | 2/2009 | Urlaub et al. | |
| 7,531,471 B2 | 5/2009 | Quincy, III | |
| 7,655,829 B2 | 2/2010 | MacDonald et al. | |
| 7,690,514 B2 | 4/2010 | McKeown et al. | |
| 7,794,737 B2 | 9/2010 | Fish et al. | |
| 7,806,962 B2 | 10/2010 | Liu et al. | |
| 7,879,350 B2 | 2/2011 | MacDonald et al. | |
| 7,906,223 B2 | 3/2011 | Rakow et al. | |
| 7,915,363 B2 | 3/2011 | Funk et al. | |
| 8,067,110 B2 * | 11/2011 | Rakow | G01N 21/783 |
| | | | 429/119 |
| 8,168,852 B2 | 5/2012 | Quincy, III | |
| 8,287,510 B2 * | 10/2012 | MacDonald | A61F 13/5514 |
| | | | 106/31.13 |
| 8,409,618 B2 | 4/2013 | MacDonald et al. | |
| 8,623,928 B2 | 1/2014 | Du et al. | |
| 8,685,178 B2 | 4/2014 | Do et al. | |
| 8,771,661 B2 | 7/2014 | MacDonald | |
| 2004/0127877 A1 | 7/2004 | Odorzynski et al. | |
| 2006/0129114 A1 | 6/2006 | Mason et al. | |
| 2006/0271002 A1 * | 11/2006 | Botten | A61F 5/441 |
| | | | 604/333 |
| 2007/0180998 A1 * | 8/2007 | Arnold | F17C 11/005 |
| | | | 96/108 |
| 2007/0209505 A1 | 9/2007 | Liu et al. | |
| 2008/0200890 A1 | 8/2008 | Wood et al. | |
| 2010/0166817 A1 | 7/2010 | Shen | |
| 2011/0087185 A1 | 4/2011 | Woehlke et al. | |
| 2011/0112496 A1 | 5/2011 | Fukae et al. | |
| 2011/0124755 A1 * | 5/2011 | Zhang | C08G 18/022 |
| | | | 521/128 |
| 2011/0282309 A1 * | 11/2011 | Adie | A61F 13/022 |
| | | | 604/319 |
| 2012/0101862 A1 | 4/2012 | Stanton | |
| 2013/0203699 A1 | 8/2013 | Nonni et al. | |
| 2014/0021967 A1 | 1/2014 | Kang et al. | |
| 2014/0249495 A1 * | 9/2014 | Mumby | A61F 13/0206 |
| | | | 604/359 |
| 2014/0255636 A1 * | 9/2014 | Odeh | B01D 71/58 |
| | | | 428/36.5 |
| 2014/0309947 A1 | 10/2014 | Gryska et al. | |
| 2015/0109003 A1 * | 4/2015 | Palazzotto | G01N 27/22 |
| | | | 324/658 |
| 2016/0367948 A1 * | 12/2016 | Song | C08J 9/36 |

FOREIGN PATENT DOCUMENTS

| | | |
|---|---|---|
| EP | 2 284 219 A1 | 2/2011 |
| EP | 2 192 146 B1 | 12/2011 |
| EP | 2 423 241 A1 | 2/2012 |
| RU | 2448129 C2 | 4/2012 |
| WO | 2005012397 A2 | 2/2005 |
| WO | WO 2005/120594 A1 | 12/2005 |
| WO | 2007038966 A1 | 4/2007 |
| WO | 2008007557 A1 | 1/2008 |
| WO | WO 2012/016634 A1 | 2/2012 |
| WO | WO 2014/078914 A1 | 5/2014 |

OTHER PUBLICATIONS

Budd, Peter M. et al., "A nanoporous network polymer derived from hexaazatrinaphthylene with potential as an absorbent and catalyst support" Journal of Material Chemistry, vol. 13, No. 11, Nov. 2003, pp. 2653-2844.

Budd, Peter M. et al., "Polymers of intrinsic microporosity (PIMS): robust, solution-processable, organic nanoporous materials" Chemical Communications, No. 2, Jan. 21, 2004, pp. 127-251.

Jeffs, Corinne A. et al., "A polymer of intrinsic microporosity as the active binder to enhance absorption/separation properties of composite hollow fibres" Microporous and Mesoporous Materials, 170, 2003, pp. 105-112.

Maffei, A. Verena et al., "Adsorption Studies of a Microporous Phthalocyanine Network Polymer" Langmuir, Feb. 9, 2006, 22, pp. 4225-4229.

McKeown, Neil B., "Polymers of Intrinsic Microporosity" International Scholarly Research Network, vol. 2012, Article ID 513986, 16 pages.

Song, Qilei et al., "Controlled thermal oxidative crosslinking of polymers of intrinsic micoporosity towards tunable molecular sieve membranes" Nature Communications, Sep. 4, 2014, DOI: 10.1038/ncomms5813.

* cited by examiner

ODOR CONTROL ARTICLE

TECHNICAL FIELD

Hydrophobic polymers of intrinsic porosity and their use for odor control in personal care product and hygienic product applications are described.

BACKGROUND OF THE DISCLOSURE

The present disclosure involves the control or reduction of odors in personal care products and hygienic products. Odors can result from various liquid and solid waste discharged from the body of humans or animals, such as, for example, urine, feces, blood and/or sweat. The reduction or elimination of odors due to the bodily waste is of particular interest for the user or wearer of the personal care product in order to avoid embarrassment. Personal care products can be placed against or in proximity to the body (i.e., contiguous with the body) of a wearer and non-limiting examples can include, for example, diapers, diaper pants, training pants, swimwear, absorbent underpants, adult incontinence products including garments and insert pads, bed pads, feminine hygiene pads or liners, tampons, sweat absorbing pads, shoe pads, helmet liners, body wipes, tissues, towels, napkins, and the like, as well as medical articles such as medical absorbent garments, bandages, masks, wound dressings, surgical bandages and sponges, underpads, and the like.

Hygienic products can include articles that may be used to preserve the health of a user that is, for example, by providing cleanliness or a sense of cleanliness, such as for example through the control of odors, and can include articles that are not placed against or used in proximity of the body of a user. For example, in a kitchen environment, blood or juices from meat or other foods may pool in a refrigerator or on a surface, such as, for example, a shelf or a countertop. Odor can generate as a byproduct of bacteria feeding and living on the blood or juices or from the spoiling of food. Odors can also generate from various foods that often emit strong aromas, such as from garlic, cheeses, meats and/or spices. Thus, it is desirable that hygienic products have odor-controlling properties. Non-limiting examples of hygienic products can include, for example, refrigerator pads, surface wipes (to clean counters, mirrors, etc.), odor-absorbing sheets, trash can liners, and the like. Odor-absorbing sheets can also be useful for air vent or filter applications, such as for example, kitchen exhaust fans or cat litter box air filters.

Two approaches commonly used with personal care products and hygienic products to control odor include masking the odor with fragrance and absorbing the odor with an odor-absorbing material such as a cyclodextrin or activated carbon. Drawbacks of masking odor with fragrance include the use of fragrances where the scent is not acceptable to the user and/or using an amount of fragrance that inadequately masks the amount of odor.

Cyclodextrin-based materials have limited odor-absorbing capacities due to, 1) weak binding strengths with some odorous compounds and, 2) generally not absorbing odorous compounds effectively while in solid state. Activated carbon is aesthetically unpleasing due to the black color even though it provides effective odorant absorption. Activated carbon is generally avoided in personal care products that touch the body in use, such as for example, a diaper or a feminine hygiene pad, for likelihood of the user suspecting that, 1) the product is dirty, 2) is unsafe for use, or 3) has some other defect. Furthermore, activated carbon cannot be easily used in various types of films or coatings.

Thus, there remains a need in personal care products and hygienic products for an odor-controlling material that is aesthetically acceptable to the user and simple to process.

SUMMARY OF THE DISCLOSURE

In one aspect, the disclosure includes an odor control article. The odor control article includes a hydrophobic polymer of intrinsic microporosity. The hydrophobic polymer of intrinsic microporosity can absorb odorous compounds such as volatile aldehydes, volatile ketones, volatile fatty acids, volatile amine derivatives, volatile sulfur derivatives, thiol derivatives and combinations thereof. The hydrophobic polymer of intrinsic microporosity includes a colorant wherein a ratio of the colorant to the hydrophobic polymer of intrinsic microporosity by weight is from 0.001 to 0.30.

In another aspect, a method of making an odor control suspension is disclosed. The method includes dissolving a hydrophobic polymer of intrinsic microporosity in an organic solvent to form a mixture. The mixture is then added to an aqueous solution to form an odor control solution. The odor control solution is mixed. The organic solvent is removed from the odor control solution to form an odor control suspension.

In a further aspect, an odor-absorbing member is disclosed. The odor-absorbing member includes a substrate that has a surface. The substrate can be a plurality of particles, a plurality of fibers, a film, a nonwoven web, or combinations thereof. The odor-absorbing member also includes an odor control article having a hydrophobic polymer of intrinsic microporosity and a colorant. The ratio of the colorant to the hydrophobic polymer of intrinsic microporosity by weight is from 0.001 to 0.3. The odor control article is disposed on the substrate surface and/or within the substrate.

Figure 5A:
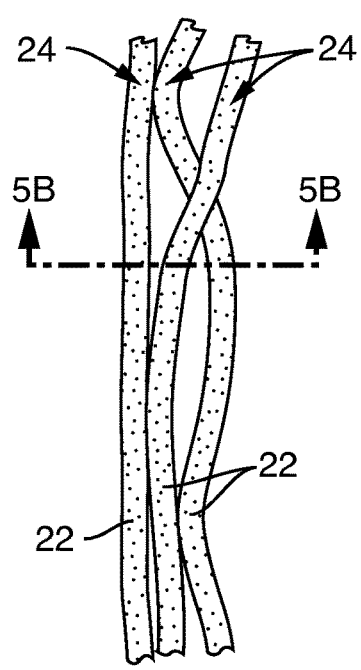
FIG. 5A representatively illustrates the odor control article coated on cellulosic fibers.
Figure 5C:
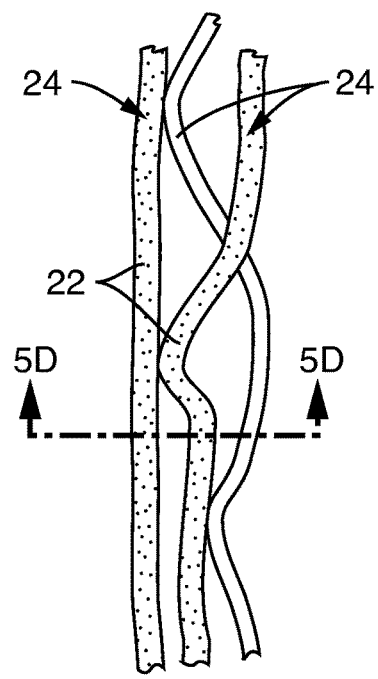
FIG. 5C representatively illustrates the odor control article coated on some of the cellulosic fibers.
Figure 5B:
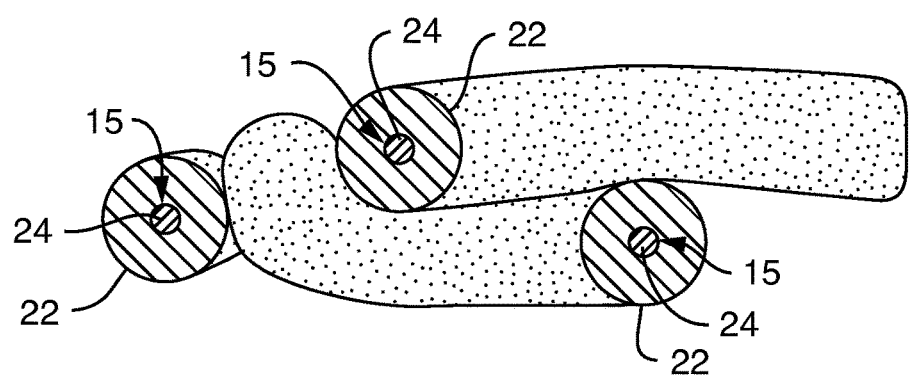
FIG. 5B representatively illustrates a cross section of the odor control article coated on the cellulosic fibers taken at line 5B-5B of FIG. 5A.
Figure 5D:
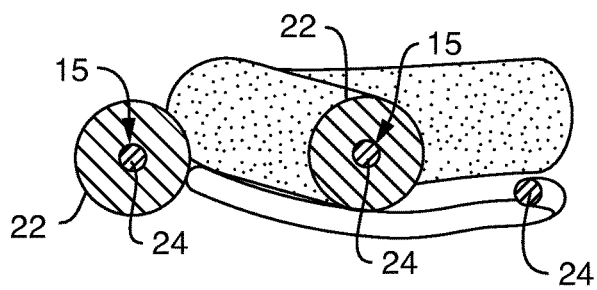
FIG. 5D representatively illustrates a cross section of the odor control article coated on some of the cellulosic fibers taken at line 5D-5D of FIG. 5C.
Figure 5E:
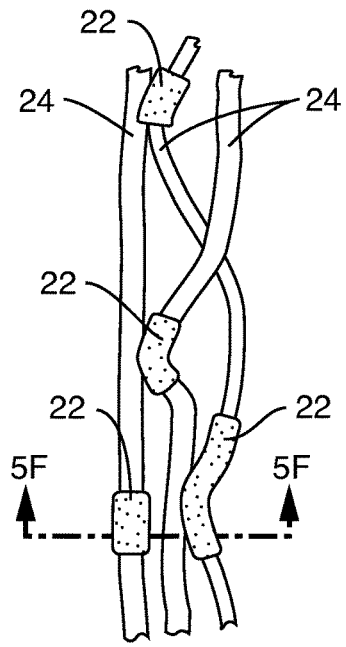
FIG. 5E representatively illustrates the odor control article coated on portions of the cellulosic fibers.
Figure 5F:
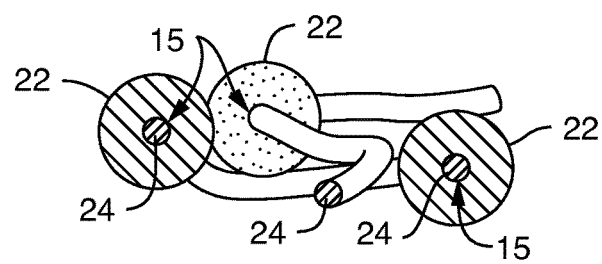

s FIG. 5F representatively illustrates a cross section of the odor control article coated on portions of the cellulosic fibers taken at line 5F-5F of FIG. 5E.

Figure 5G:
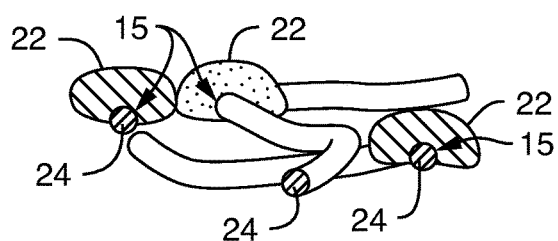

FIG. 5G representatively illustrates a cross section of an alternate configuration of the odor control article coated on portions of the cellulosic fibers taken at line 5F-5F of FIG. 5E.

Figure 6:
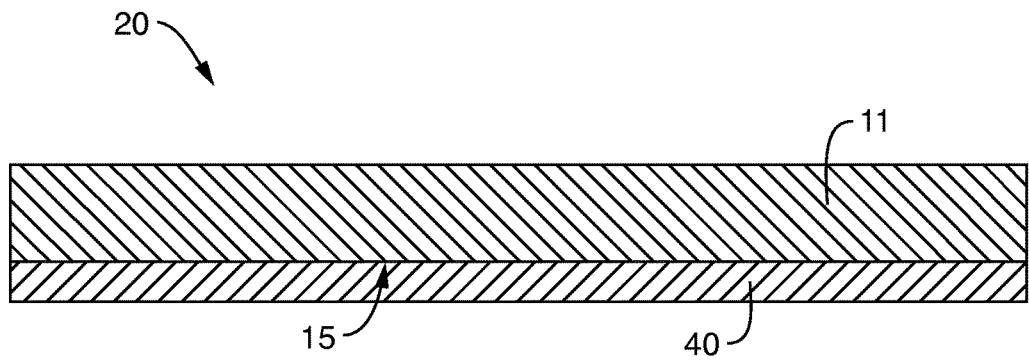
Figure 7A:
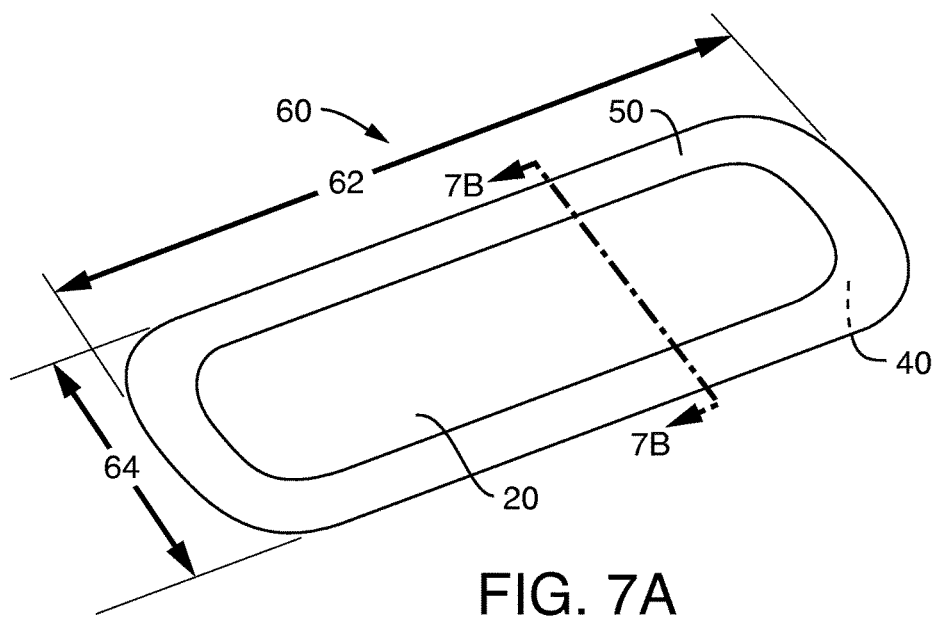

FIG. 6 representatively illustrates an odor-absorbing member disposed on a barrier sheet. FIG. 7A representatively illustrates an incontinence pad.

Figure 7B:
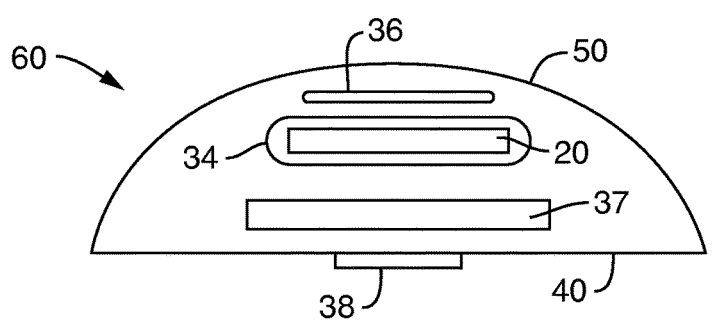

FIG. 7B representatively illustrates a schematic cross section of the incontinence pad 60 taken at line 7B-7B of FIG. 7A.

FIG. 8A-FIG. 8E representatively illustrates various dispositions of an odor-absorbing member relative to a barrier sheet.

Figure 9A:
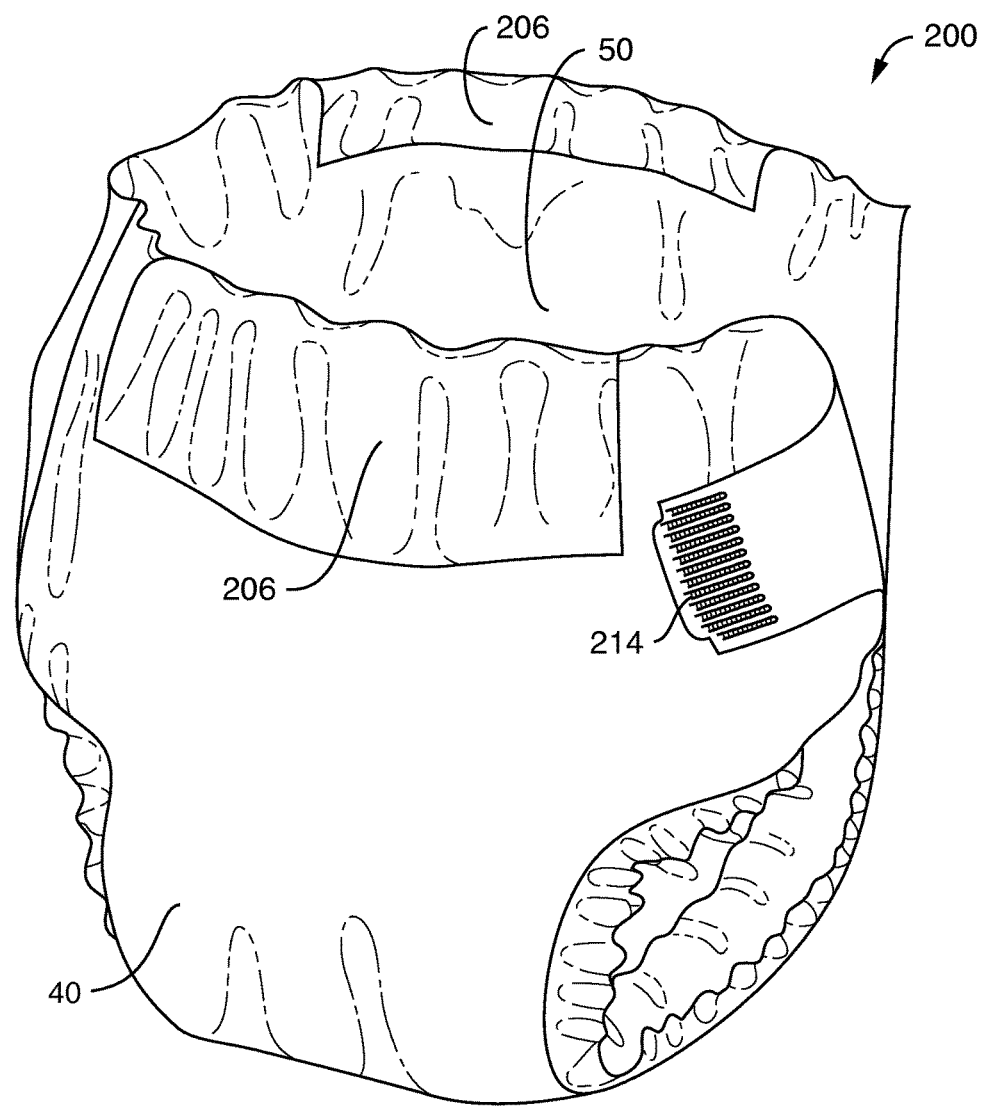

FIG. 9A representatively illustrates a perspective view of a diaper.

Figure 9B:
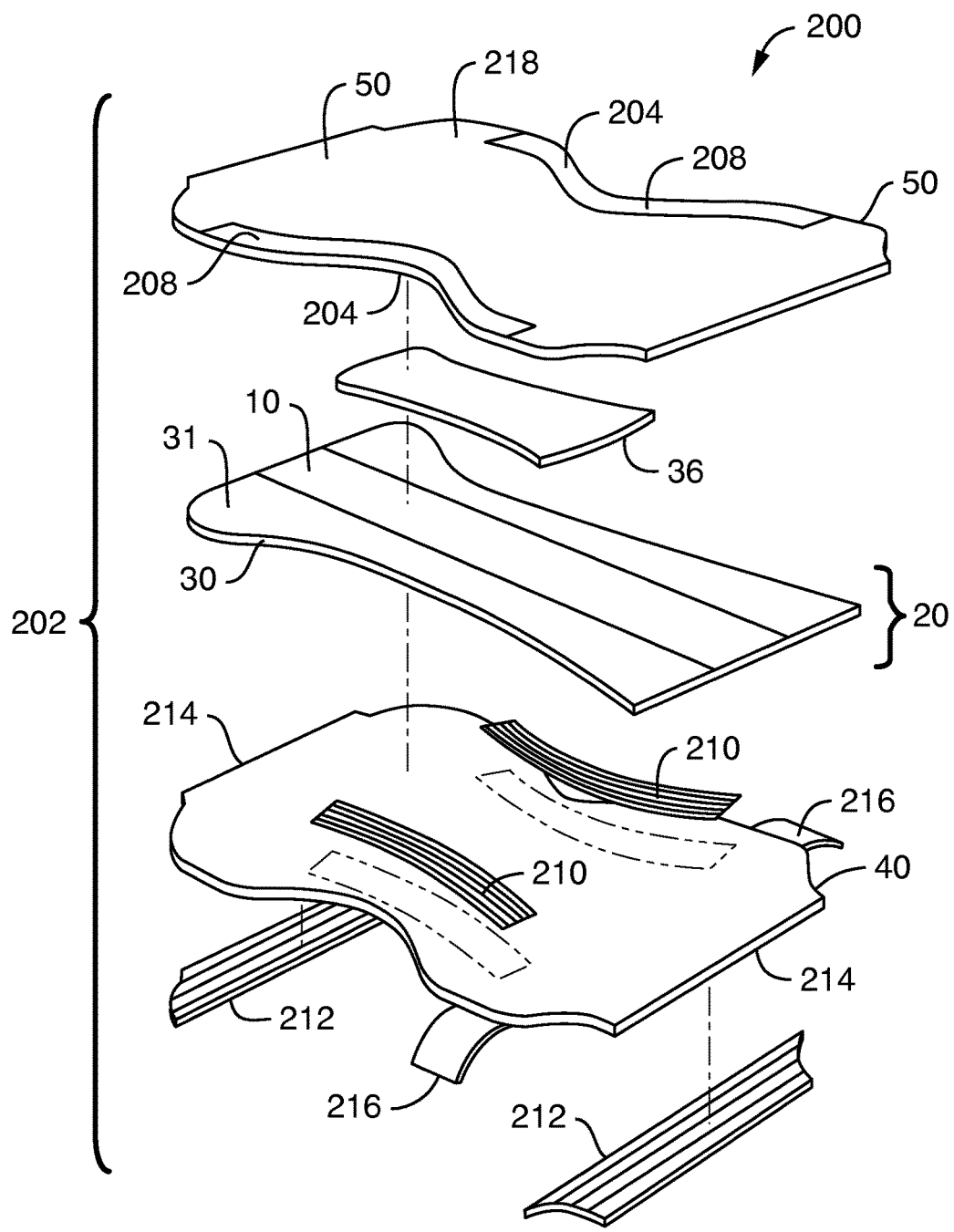

FIG. 9B representatively illustrates an exploded view of the diaper of FIG. 9A.

Repeat use of reference characters in the present specification and drawings is intended to represent the same or analogous features or elements of the disclosure.

DETAILED DESCRIPTION OF THE DISLOSURE

The term "carded web" refers herein to a web containing natural or synthetic staple length fibers typically having fiber lengths less than about 100 mm. Bales of staple fibers can undergo an opening process to separate the fibers which are then sent to a carding process which separates and combs the fibers to align them in the machine direction after which the fibers are deposited onto a moving wire for further processing. The web is usually subjected to some type of bonding process such as thermal bonding using heat and/or pressure, ultrasonic bonding, or may be subject to adhesive processes to bind the fibers together. The carded web may be subjected to fluid entangling, such as hydroentangling, to further intertwine the fibers and thereby improve the integrity of the carded web.

The term "coform" refers herein to a blend of meltblown fibers and absorbent fibers such as cellulosic fibers that can be formed by air forming a meltblown polymer material while simultaneously blowing air-suspended fibers into the stream of meltblown fibers. The meltblown fibers and absorbent fibers are collected on a forming surface, such as provided by a belt. Two U.S. patents describing coform materials are U.S. Pat. No. 5,100,324 to Anderson et al. and U.S. Pat. No. 5,350,624 to Georger et al., both of which are incorporated in their entirety in a manner consistent herewith.

The term "film" refers herein to a thermoplastic film made using an extrusion and/or forming process, such as a cast film or blown film extrusion process. The term includes apertured films, slit films, and other porous films which constitute liquid transfer films, as well as films which do not transfer fluids, such as, but not limited to, barrier films, filled films, breathable films, and oriented films. The term may even include liquid absorbent films.

The term "hygienic product" refers herein to an article that may be used to preserve the health of a user that is, for example, by providing cleanliness or a sense of cleanliness. Non-limiting examples of articles that may be used to preserve the health of a user include, for example, refrigerator pads, surface wipes (to clean counters, mirrors, etc.), odor absorbing sheets, trash can liners, and the like.

The term "meltblown" refers herein to fibers formed by extruding a molten, thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface or support to form a web of randomly dispersed meltblown fibers. Such a process is disclosed, for example in U.S. Pat. No. 3,849,241 to Butin et al. which is incorporated herein by reference in its entirety in a manner consistent herewith.

The terms "nonwoven" and "nonwoven web" refers herein to materials and webs of material that are formed without the aid of a textile weaving or knitting process. For example, nonwoven materials, fabrics or webs have been formed from many processes such as, for example, meltblowing processes, spunbonding processes, air laying processes, coform processes, and bonded carded web processes, and can include webs formed of combinations thereof.

The term "personal care product" refers herein to an article that may be placed against or in proximity to the body (i.e., contiguous with the body) of a wearer to absorb and contain various liquid and solid waste discharged from the body. Non-limiting examples of articles that may be placed against or in proximity to the body include, for example, diapers, diaper pants, training pants, swimwear, absorbent underpants, adult incontinence products including garments and insert pads, bed pads, feminine hygiene pads or liners, digital tampons, sweat absorbing pads, shoe pads, helmet liners, wipes, tissues, towels, napkins, and the like, as well as medical absorbent articles such as medical absorbent garments, bandages, masks, wound dressings, surgical bandages and sponges, underpads, and the like.

The term "spunbonded fibers" refers herein to small diameter fibers which are formed by extruding molten thermoplastic material as filaments from a plurality of fine, usually circular-capillaries of a spinneret with the diameter of the extruded filaments then being rapidly reduced to fibers as by, for example, in U.S. Pat. No. 4,340,563 to Appel et al.; U.S. Pat. No. 3,692,618 to Dorschner et al.; U.S. Pat. No. 3,802,817 to Matsuki et al.; U.S. Pat. Nos. 3,338,992 and 3,341,394 to Kinney; U.S. Pat. No. 3,502,763 to Hartman; and U.S. Pat. No. 3,542,615 to Dobo et al., the contents of which are incorporated herein by reference in their entirety in a manner consistent herewith.

The term "thermoplastic" refers herein to a material which softens and which can be shaped when exposed to heat and which substantially returns to a non-softened condition when cooled.

The present disclosure involves the control of odors in personal care products and hygienic products. The personal care products and hygienic products may be configured to absorb liquid and be referred to as liquid absorbent articles. Odors associated with the use of personal care products can emanate from components of bodily exudates, such as, for example, urine, feces, sweat, menses, or blood. For example, urine, after being voided from the body and for a time thereafter, includes volatile organic compounds such as aldehydes, which present odor associated with urine. Odors associated with feces may include sulfide, thiol and indole volatiles, such as, for example, methyl sulfides, methanethiol, dimethyl disulfide, dimethyl trisulfide, skatole, and benzopyrrole. Odors associated with sweat may include aldehydes, such as, for example, decanal, undecanal, nonanal and nonenal, C6 to C11 normal, branched and unsaturated aliphatic acids, alcohols, carbonyls, amines, such as, for example, triethylamine, and some steroids. Odors associated with menses may include aldehydes, ketones, aromatics, alcohols, acids, esters, phenolics, pyrazines, and amines.

Odors associated with the use of hygienic products may include some of the odors associated with personal care products and may additionally include those associated with food. For example, the pungent aroma of garlic is associated with diallyl disulfide, allyl methyl sulfide, allyl mercaptan, and allyl methyl disulfide. The odors associated with rosemary oil include α-pinene, β-pinene, camphene, 1,8-cineole, camphor, and linalool. Odors associated with cheese may include volatile fatty acids and lactones. Other foods may include odors associated with ketones, such as, for example, 2,3-butanedione. In general, malodorous gases or compounds associated with bodily exudates or food may include volatile aldehydes, volatile ketones, volatile fatty acids, volatile amine derivatives, volatile sulfur derivatives, volatile thiol derivatives, and combinations thereof.

The subject application discloses hydrophobic polymers of intrinsic porosity (HPIMs) for the control of odors in personal care products and hygienic products. While HPIMs for odor control in personal care products and hygienic products may have similar odor absorption capacity as activated carbon, the HPIMs are easier to incorporate into personal care products and hygienic products than activated carbon. Furthermore, the HPIMs that have a colorant added through the use of pigments or dyes can make the personal care product or the hygienic product more aesthetically pleasing to the user. The colorant will have little or no effect on the odor-absorbing capacity of the HPIM. The HPIMs generally have pleasant hues and are more aesthetically pleasing to the user than the black color of activated carbon even when colorant is not added.

HPIMS are characterized by microporosity that is derived from the molecular structures of the polymer (intrinsic) as opposed to introducing pores through processing steps after the polymer is formed (extrinsic). The HPIMs can include a pore volume of at least 0.1 ml/g as measured by nitrogen adsorption under cryogenic conditions using the Brunauer, Emmett and Teller (BET) method. The polymeric material can have at least about 25% of the total pore volume as measured by nitrogen adsorption, resulting from pores having a diameter in the range of less than about 100 nanometers, and more specifically from about 0.3 nanometers to about 20 nanometers.

The surface area of the HPIMs, as measured by nitrogen adsorption or a related technique, may be at least about 300 $m^2g^{-1}$, wherein the actual value is dependent upon the specific monomer. The surface area of the HPIMs can range from about 500 to about 1500 $m^2g^{-1}$.

Regarding molar mass distribution, the HPIMs can have, 1) a number average molecular weight, $M_n$, in the range from about 1 kilo-Dalton (kDa) to about 3.2 kDa, 2) a weight average molecular weight, $M_w$, in the range from about 1 kDa to about 17.7 kDa, 3) an average molar mass, $M_z$, in the range from about 1 kDa to about 361 kDa, and 4) a dispersity ($M_w/M_n$) of about 6. These molar mass averages, $M_n$, $M_w$ and $M_z$, include the oligomeric and polymeric structures of HPIMs as measured by Gel Permeation Chromatography (GPC).

The HPIMs may include those of non-network polymers that have a chain of repeating units bonded to each other and each including a first generally planar species and a rigid linker. The rigid linker has a point of contortion such that two adjacent first planar species connected by a rigid linker are held in lo a non-coplanar orientation. The polymer being such that said repeating units include a first generally planar species and the rigid linker are bonded predominately to two other such repeating units. The intrinsic nanopores of the HPIMs will not collapse due to the HPIM rigid structure. Non-limiting examples of HPIMs that are within the scope of the present disclosure include repeating units of any of the following formulas designated as PIM-1, known as polydioxane A, PIM-2, PIM-3, and PIM-4:

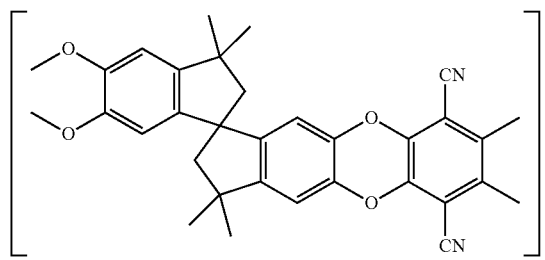

PIM-1

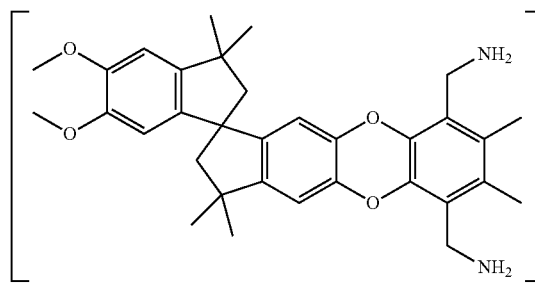

PIM-2

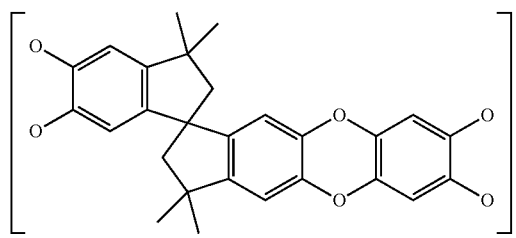

PIM-3

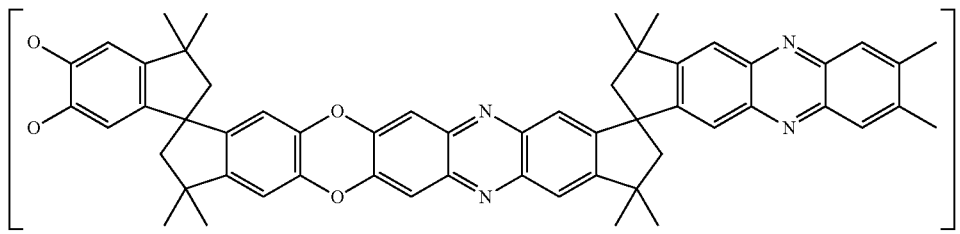

PIM-4

The formulas may include optional substituents. Referring to the PIM-1 formula, the cyano groups (CN) are optional substituents, meaning that the cyano groups may be omitted or may be replaced with other substituents. For example, as shown in the formula of PIM-2, amino groups ($NH_2$) have replaced the cyano groups of PIM-1.

After the HPIM polymer has been synthesized, it can be further processed into a plurality of particles, a plurality of fibers, or combinations thereof.

The HPIM is integrated with a colorant to form an odor control article. The colorant can be a pigment, an organic dye, or combinations thereof. Non-water soluble organic dyes and pigments are preferred for the personal care products and the hygienic products. Non-limiting examples of suitable pigments include: 1) cadmium pigments such as cadmium yellow, cadmium red, cadmium green, cadmium orange, and cadmium sulfoselenide, 2) chromium pigments such as chrome yellow and chrome green, 3) cobalt pigments such as cobalt violet, cobalt blue, cerulean blue, and aureolin (cobalt yellow), 4) copper pigments such as azurite, Han purple, Han blue, Egyptian blue, malachite, Paris green, Phthalocyanine Blue BN, Phthalocyanine Green G, verdigris, and viridian, 5) iron oxide pigments such as sanguine, caput mortuum, oxide red, red ochre, Venetian red, and Prussian blue, 6) lead pigments such as lead white, cremnitz white, Naples yellow, and red lead, 7) manganese pigments such as manganese violet, 8) mercury pigments such as vermilion, 9) titanium pigments such as titanium yellow, titanium beige, titanium white, and titanium black, 10) zinc pigments such as zinc white and zinc ferrite, 11) pigments of biological origins such as alizarin (synthesized), alizarin crimson (synthesized), gamboge, cochineal red, rose madder, indigo, Indian yellow, and Tyrian purple, and 12) non-biological, organic pigments such as quinacridone, magenta, phthalo green, phthalo blue, pigment red 170, and diarylide yellow.

Non-limiting examples of suitable organic dyes include: 1) acridine dyes that are derivatives of acridine, 2) anthraquinone dyes that are derivatives of anthraquinone, 3) arylmethane dyes, 4) diarylmethane dyes that are derivatives diphenyl methane, 5) triarylmethane dyes that are derivatives of triphenylmethane, 6) azo dyes that are based on the —N=N— azo structure, 7) diazonium dyes that are derivatives diazonium salts, 8) nitro dyes that include a —$NO^2$ nitro functional group, 9) nitroso dyes that include a —N=O nitroso functional group, 10) phthalocyanine dyes that are derivatives of phthalocyanine, 11) quinone-imine dyes that are derivatives of quinone, 12) azin dyes, 13) eurhodin dyes, 14) safranin dyes that are derivatives of safranin, 14) indamins, 15) indophenol dyes that are derivatives of indophenol, 16) oxazin dyes that are derivatives of oxazin, 17) oxazone dyes that are derivatives of oxazone, 18) tiazine dyes that are derivatives of thiazine, 19) thiazole dyes that are derivatives of thiazole, 20) xanthene dyes that are derived from xanthene, 21) fluorene dyes that are derivatives of fluorine, 22) pyronin dyes, 23) fluorone dyes that are derivatives fluorine, and 24) rhodamine dyes that are derivatives of rhodamine.

Figure 1A:
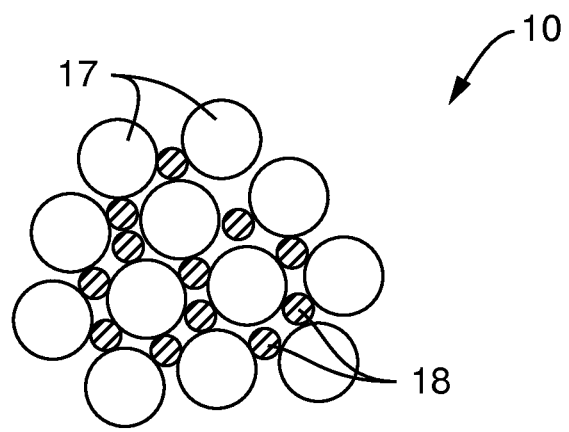
FIG. 1A representatively illustrates organic dye molecules with hydrophobic polymer of intrinsic microporosity particles.

Without being bound by theory, there may be two possible mechanisms by which the colorant and the HPIM integrate. The organic dye colorant is an individual molecule. Referring to FIG. 1A, organic dye molecules 18, due to their small size, are able to be homogeneous in solution with HPIM particles 17 to provide color to the odor control article 10; that is, there are the same proportions of the organic dye molecules 18 and the HPIM particles 17 throughout a given sample of the odor control article 10.

Figure 1B:
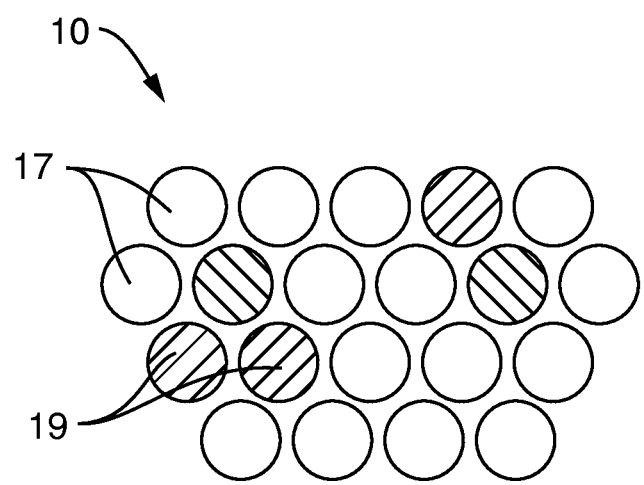
FIG. 1B representatively illustrates pigment particles with hydrophobic polymer of intrinsic microporosity particles.

The pigment colorant is an individual particle that imparts color to the odor control article 10 through phase separation with the HPIM particles 17. While referring to FIG. 1B, the pigment particles 19 are embedded with the HPIM particles 17 due to the intermolecular forces between the two different types of particles wherein there are not the same proportions of the pigment particles 19 and the HPIM particles 17 throughout a given sample of the odor control article 10.

The odor control article 10 may have a ratio of colorant to the HPIM, by weight, from about 0.001 to about 0.3, or about 0.005 to about 0.05, or about 0.2. In general, the ratio of the colorant to the HPIM may be less than 0.05 if the colorant is an organic dye and is homogeneously distributed in the network of the HPIM. Excess organic dye in the odor control article 10 may block some of the pores of the HPIM such that the odor absorption capacity is reduced. However, if a pigment is used, the ratio of the colorant to the HPIM can be as high as 0.3.

The odor control article 10 can further include an active. The active may eliminate or prevent further generation of odorous compounds or may chemically catalyze conversion of the odorous compounds into new compounds. Non-limiting examples of the active include an antimicrobial agent, an enzyme inhibitor, a fragrance, such as, for example, an odor-neutralizing fragrance, a plurality of metal ion-coated nanoparticles, or a combination thereof.

Metal ion-coated nanoparticles can include silica nanoparticles that are coated with metal ions such as copper, iron, or manganese. Examples include AVEHO metal ion-coated nanoparticles available from UltraTech International, Inc., Jacksonville, Fla., USA, or metal ion-coated nanoparticles as disclosed, for example in U.S. Pat. No. 7,976,855 to MacDonald et al. or U.S. Pat. No. 8,066,956 to Do et al., which are incorporated herein by reference in its entirety in a manner consistent herewith.

The spherical form of the metal ion-coated nanoparticle can provide a high surface area for maximum interaction between the metal and odorous compounds. Specific metals can be selected based on the target odor compound; for example, copper complexes with odor molecules such as mercaptans, amines and ammonia.

Metal ion-coated nanoparticles cannot form films or coatings and can be combined with polymer binders to form odor-absorbing films or coatings. However, many polymer binders block a portion of the active sites, or pores, of the metal ion-coated nanoparticles such that the absorption capacity is diminished.

Metal ion-coated nanoparticles can be combined with HPIM particles to form an odor control article 10 such that the absorption capacity can be minimally affected. The metal ion-coated nanoparticles are embedded with the HPIM particles through intermolecular forces between the two different types of particles. The large surface area and the rigid structure of the HPIM particles can immobilize the metal ion-coated nanoparticles without negatively affecting odor absorption capacity as the non-collapsing structure of the HPIM particles allow the metal ion-coated nanoparticles to remain active. The HPIM particles may also chemically immobilize the metal ion-coated nanoparticles through covalent attachment. The HPIM particles, through immobilization of the metal ion-coated nanoparticles, serve as binders to form porous films or coatings such that volatile odorous compounds can penetrate through the binder to access the active sites of the metal ion-coated nanoparticles. Additionally, the films or coatings may be cross-linked through irradiation-triggered processes or thermo-triggered processes.

Figure 2A:
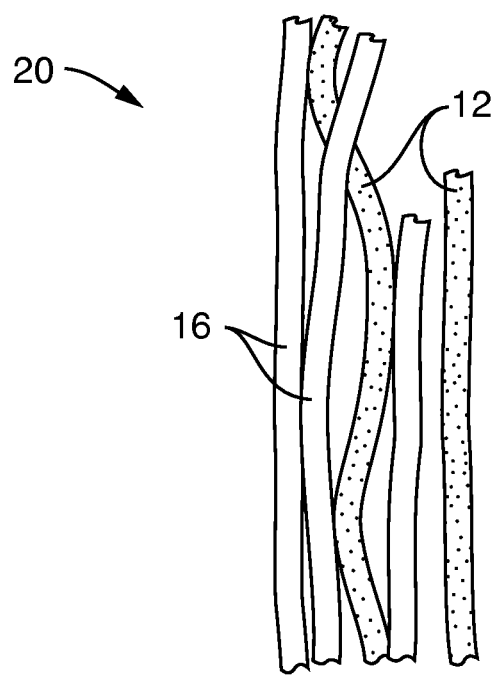
FIG. 2A representatively illustrates an odor control article in the form of fibers integrated with non-odor-controlling fibers.
Figure 2B:
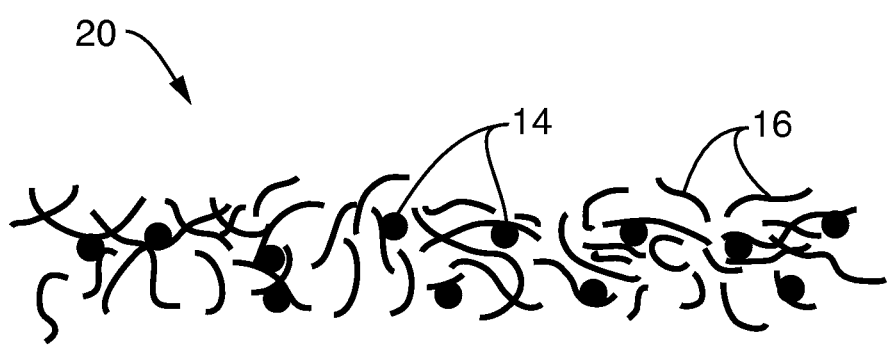
FIG. 2B representatively illustrates an odor control article in the form particles integrated with non-odor-controlling fibers.

The odor control article 10 may be integrated with a substrate to form an odor-absorbing member. The substrate can be a plurality of particles, a plurality of fibers, a film, a nonwoven web, or combinations thereof. For example, the odor-absorbing member may have the odor control article 10 intermingled with the substrate, such as, for example, when the odor control article 10 is in a form of a plurality of odor control article fibers or in a form of a plurality of odor control particles, and when the substrate is in a form of a plurality of substrate fibers or substrate particles. For example, referring to FIG. 2A, the odor-absorbing member 20 may include odor control article fibers 12 intermingled with substrate fibers 16. Referring to FIG. 2B, the odor-absorbing member 20 may also include odor control article particles 14 intermingled with substrate fibers 16.

Figure 3A:
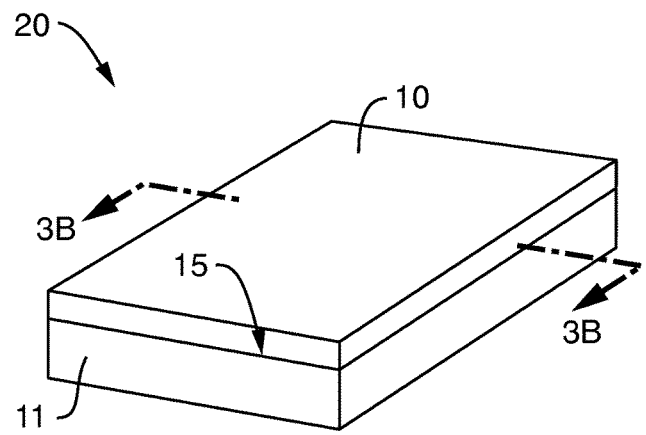
FIG. 3A representatively illustrates an odor control article applied as a continuous coating to one surface of a substrate.
Figure 3B:
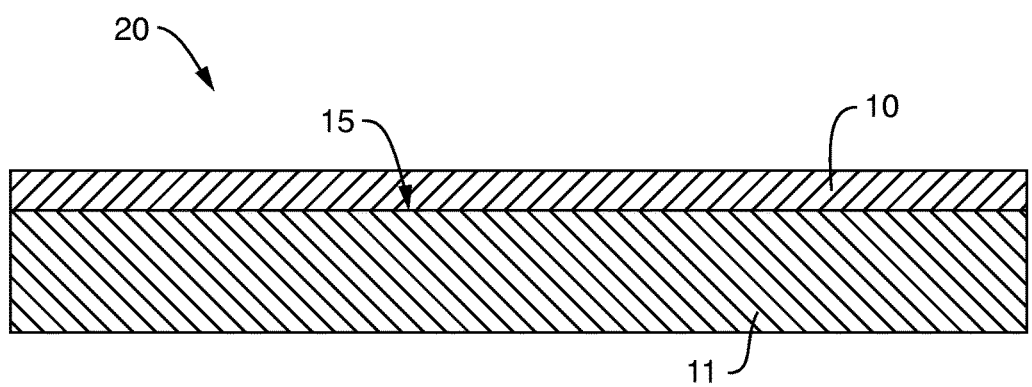
FIG. 3B representatively illustrates a cross section of the odor control article continuously coated on the substrate taken at line 3B-3B of FIG. 3A.
Figure 4A:
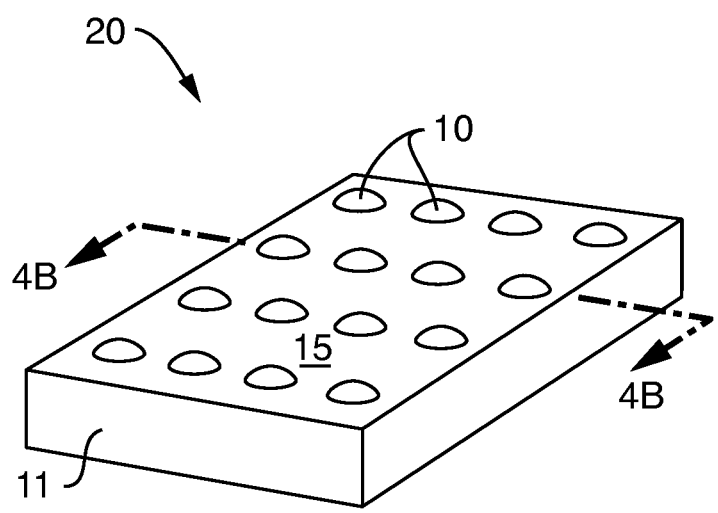
FIG. 4A representatively illustrates an odor control article applied as a discontinuous coating to one surface of a substrate.
Figure 4B:
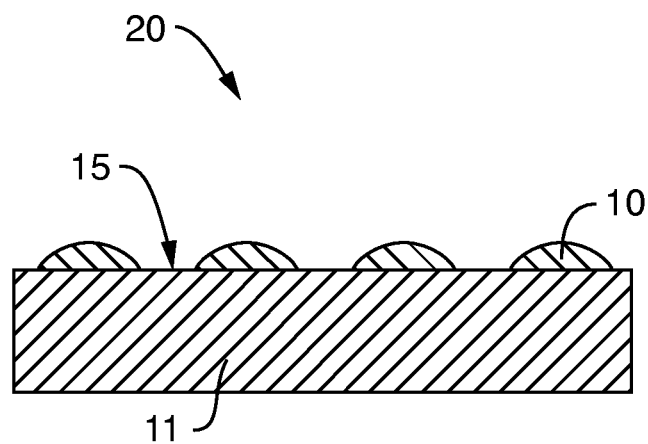
FIG. 4B representatively illustrates a cross section of the odor control article discontinuously coated on the substrate taken at line 4B-4B of FIG. 4A.

Referring to FIG. 3A-4B, the odor control article 10 may be applied to the substrate 11, such as, for example, a film or a nonwoven web, by coating. Coating applications may include roll-coating, printing, dipping, immersing, soaking, spraying, or by any other suitable application means. The odor control article 10 may be applied to at least one substrate surface 15. Referring to FIGS. 3A and 3B, the odor control article 10 may be applied upon the substrate surface 15 as a continuous coating wherein the substrate surface 15 is completely covered by the odor control article 10. Such coverage may be at a uniform thickness, as shown. Referring to FIG. 4A and FIG. 4B, the odor control article 10 can also be applied as a discontinuous coating onto the substrate 11. A portion or portions of the substrate surface 15 may be covered by the odor control article 10, possibly forming a pattern. Any pattern is possible. It may form indicia such as letters, numbers or geometric shapes.

In one aspect, the substrate 11 of the odor-absorbing member 20 is a liquid absorbent member because the substrate 11 functions to absorb liquids, such as urine, menses, fecal matter, or blood. The substrate 11 can be a plurality of fibers, a film, a nonwoven web, and combinations thereof. For example, the liquid absorbent member may be a plurality of cellulosic fibers that form a cellulosic tissue web. An example of a cellulosic tissue web is a 0.86 g KIMWIPE wiper that is a 1-ply cellulosic tissue wiper, available from Kimberly-Clark Corporation, Dallas, Tex., USA, which can be used for the wiping of hands and hard surfaces. Other exemplary substrates 11 in the form of cellulosic tissue webs include paper toweling or facial tissue.

In an aspect, a KIMWIPE wiper coated with the odor control article 10 can absorb about 90% of malodorous compounds in about 5 minutes of exposure time. For example, PIM-1 can absorb approximately (as measured by gas chromatography), 1) about 45% to about 86% by weight of dimethyl disulfide in about 5 minutes of exposure time, 2) about 39% to about 85% of 2,3-butanedione by weight in about 5 minutes and 30 seconds of exposure time, 3) about 24% to about 60% of triethylamine by weight in about 5 minutes of exposure time, and 4) about 32% to about 73% of butanal by weight in about 4 minutes and 30 seconds of exposure time.

In another aspect, PIM-1 and copper ion-coated nanoparticles coated on a KIMWIPE wiper can absorb about 50% of 2,3-butanedione by weight in about 5 minutes of exposure time. For example: 1) a coating prepared with a ratio of about 90% copper ion-coated nanoparticles to about 10% PIM-1, by weight, absorbed about 46% of 2,3-butanedione by weight; 2) a coating prepared with a ratio of about 99% copper ion-coated nanoparticles to about 1% PIM-1, by weight, absorbed about 40% of 2,3-butanedione by weight; and 3) a coating prepared with a ratio of about 80% copper ion-coated nanoparticles to about 20% PIM-1, by weight, absorbed about 50% of 2,3-butanedione by weight. Comparatively, the copper metal ion-coated nanoparticles alone, at 10% by weight, absorbed about 38% of 2,3-butanedione by weight; and the PIM-1 particles alone, at 1% by weight, absorbed about 15% of 2,3-butanedione by weight. The data indicates that the PIM-1 particles minimally affect the absorption capacity of the copper ion-coated nanoparticle, if at all.

The substrate 11 can include additional material. An example of a substrate 11 including non-liquid absorbent fibers and a liquid absorbent member is coform, which includes meltblown and cellulosic fibers, respectively. In another example, the substrate 11 that is a liquid absorbent member is a combination of two or more liquid absorbent materials, such as, for example, cellulosic fibers and superabsorbent particles. In one aspect, the odor control article 10 is in the form of an odor control particle coating and may be applied to one of the liquid absorbent materials, such as, for example, the cellulosic fibers. Shown respectively in FIGS. 5A-5G, the odor control particle coating 22 may be coated onto to all of the cellulosic fibers 24, applied to some of the cellulosic fibers 24, applied to a portion of the cellulosic fibers 24, or a combination thereof. The odor control particle coating 22 may be coated onto to all of the cellulosic fibers 24 at the substrate surface 15 as shown in FIGS. 5A-5B. The odor control particle coating 22 may be coated onto some of the cellulosic fibers 24 at the substrate surface 15 as shown in FIGS. 5C-5D. FIG. 5E shows the odor control particle coating 22 coated onto a portion of some of the cellulosic fibers 24 at the substrate surface 15. The embodiment shown in FIG. 5F shows the particle coating 22 around the entire circumference of the cellulosic fiber 24 while the embodiment shown in FIG. 5G shows the particle coating 22 on a portion of the circumference of the cellulosic fiber 24.

Referring to FIG. 6, the odor-absorbing member 20 may further include a barrier sheet 40 attached to the substrate surface 15. The barrier sheet 40 may be liquid impervious so that it blocks liquids not absorbed by the substrate 11. The barrier sheet 40 may be made from a film, such as a polyethylene or polypropylene film.

Several hygienic products may include barrier sheets 40 and a substrate 11. For example, the odor-absorbing member 20 shown in FIG. 6 may be used as a refrigerator pad. The refrigerator pad can be used with a container, a drawer or a shelf within a refrigerator to absorb spills of liquids and or odor within the container, the drawer, or on the shelf. The barrier sheet 40 may be a polypropylene film and the substrate 11 may be a coform web.

Referring now to FIGS. 7A-7B, in another aspect, the odor-absorbing member 20 may be used in personal care products. One example of a personal care product is an incontinence pad 60 having a length 62 and a width 64. The odor-absorbing member 20 may include a liquid absorbent substrate (not shown). The incontinence pad 60 includes a liquid pervious topsheet 50, which is designed to allow fluids, such as, for example, urine, blood, or runny fecal matter to quickly pass therethrough. The topsheet 50 may be made from nonwoven webs, such as, for example, polypropylene spunbonded webs or multi-component bonded carded webs.

Referring now to FIG. 7B, in some aspects, between the barrier sheet 40 and the topsheet 50 and in addition to the odor-absorbing member 20, there may be a number of layers for different purposes. Other optional layers may include an acquisition layer 36, a distribution layer 37, and a tissue wrap 34. The acquisition layer 36 may be positioned beneath the topsheet 50 and acts as a reservoir to accept large surges of liquid and slowly release them to, for example, the odor-absorbing member 20. In some aspects, wherein the substrate of the odor-absorbing member 20 further includes superabsorbent particles, the tissue wrap 34 can surround the odor-absorbing member 20 and keep the superabsorbent particles from leaving the substrate. In yet other aspects, the distribution layer 37 may be positioned beneath the tissue wrapped odor-absorbing member 20 wherein the distribution layer 37 is designed to distribute bodily exudates that are not readily absorbed upon initial contact with the odor-absorbing member 20.

The topsheet 50 is at the top and an acquisition layer 36 is positioned below the topsheet 50. Below the acquisition layer 36 is the odor-absorbing member 20 surrounded by tissue wrap 34. Distribution layer 37 is positioned below the tissue wrapped odor-absorbing member 20. The barrier sheet 40 is below the distribution layer 37. Many products also have an adhesive strip 38 placed on the outer surface of the barrier sheet 40 to help hold the product in place during use by adhering it to the user's underclothes.

Several personal care products that include barrier sheets 40, odor-absorbing members 20 and topsheets 50 may be in the form of diapers, training pants, absorbent underpants, adult incontinence products, and feminine hygiene products. It should be understood that hygienic products may also include optional layers similar to those found in personal care products, such as, for example, topsheets 50 to allow juice from foods to pass through quickly, acquisition layers 36 or distribution layers 37.

Regardless of the particular form of the personal care product or the hygienic product, the substrate of the odor-absorbing member 20 can be any layer that may be a component of the personal care product or the hygienic product, such as, for example, the topsheet 50, the barrier sheet 40, the acquisition layer 36, the distribution layer 37, the tissue wrap 34, or the liquid absorbent member. The odor-absorbing member 20 can be between the topsheet 50 and the barrier sheet 40. Referring to FIGS. 8A-8E, the odor control article 10 of the odor-absorbing member 20 can be disposed such that the odor control article 10 is disposed: 1) on the barrier sheet 40, 2) in direct contact with the barrier sheet 40, or 3) not in direct contact with the barrier sheet 40. The term "adjacent" as used herein means that components are in direct contact with each other. In one aspect shown in FIG. 8A, a personal care product 80 includes a topsheet 50 and a barrier sheet 40. The barrier sheet 40 is the substrate of the odor-absorbing member 20 such that the odor control article 10 is in direct contact with the barrier sheet 40 at substrate surface 15. The odor control article 10 is disposed between the topsheet 50 and the barrier sheet 40, and is adjacent to the topsheet 50.

Figure 8A:
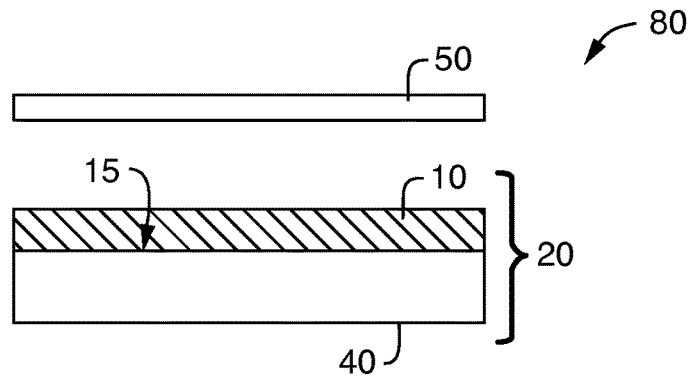
Figure 8B:
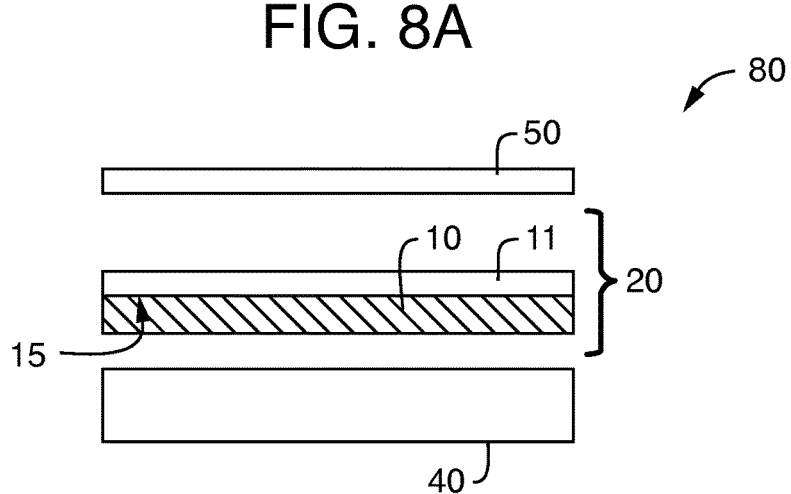

In another aspect shown in FIG. 8B, a personal care product 80 includes a topsheet 50, a barrier sheet 40 and an odor-absorbing member 20. The odor control article 10 of the odor-absorbing member 20 is in direct contact with the substrate 11 of the odor-absorbing member 20 at substrate surface 15. The odor control article 10 is disposed between the topsheet 50 and the barrier sheet 40, and is adjacent to the barrier sheet 40.

Figure 8C:
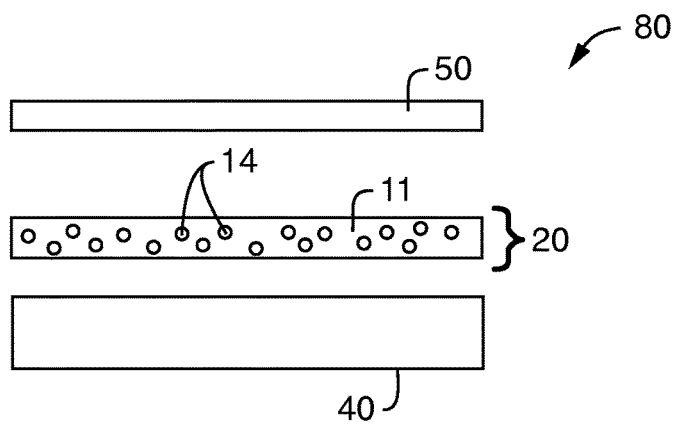

In an alternative aspect shown in FIG. 8C, a personal care product 80 includes a topsheet 50, a barrier sheet 40 and an odor-absorbing member 20. The odor-absorbing member 20 includes odor control article particles 14 such that the odor control particles 14 are intermingled within the substrate 11. The odor-absorbing member 20 is disposed between the topsheet 50 and the barrier sheet 40, and is adjacent to the barrier sheet 40.

Figure 8D:
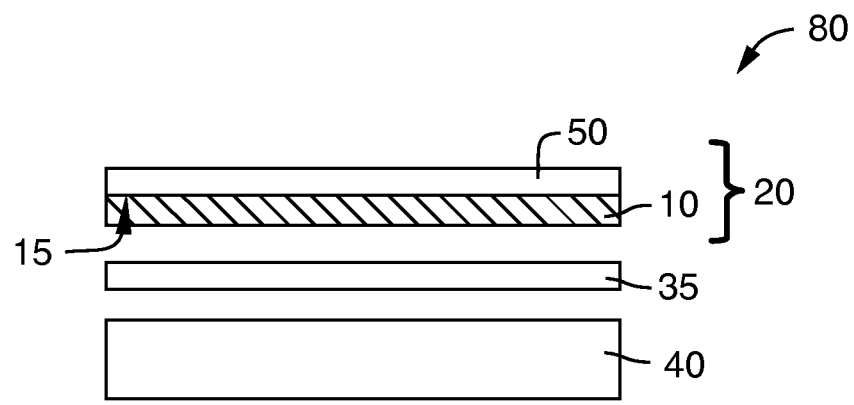

In a further aspect as shown in FIG. 8D, a personal care product 80 includes a topsheet 50, a barrier sheet 40 and at least one additional layer 35. The topsheet 50 is the substrate of the odor-absorbing member 20 such that the odor control article 10 is disposed on the topsheet 50 at substrate surface 15. The additional layer 35 is between the topsheet 50 and the barrier sheet 40. The odor control article 10 is disposed on the topsheet 50 such that the odor control article 10 is between the topsheet 50 and the barrier sheet 40, and is in direct contact with the topsheet 50.

Figure 8E:
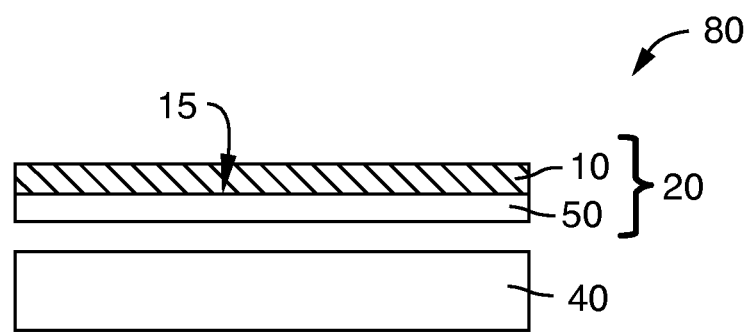

In yet another aspect as shown in FIG. 8E, a personal care product 80 includes a topsheet 50 and a barrier sheet 40. The topsheet 50 is the substrate of the odor-absorbing member 20 such that the odor control article 10 is disposed on the topsheet 50 at substrate surface 15. The odor control article 10 is in direct contact with the topsheet 50.

The subject application discloses a method of making an odor control suspension. In a dissolving step, an HPIM, such as PIM-1, is dissolved in an organic solvent to form a mixture. HPIMs are soluble in lipophilic organic solvents, but not soluble in water. Suitable organic solvents are volatile and include: 1) water miscible organic solvents, such as, for example, tetrahydrofuran, ethanol, methanol, acetone and propanol, and 2) water immiscible organic solvents, such as, for example, toluene, xylene, and benzene. A colorant can also be dissolved or suspended into the mixture.

An adding step, involves adding the mixture including the HPIM and organic solvent to an aqueous solution to form an odor control solution. A colorant may be added during the adding step. In a mixing step, the odor control solution is further mixed, such as, for example, through stirring, injecting, shaking, or agitating. It has been discovered that the use of a surfactant in the aqueous solution helps to stabilize the HPIM particles in the aqueous solution without significantly blocking the pores of the HPIM. Any surfactant may be used, including, ionic surfactants, such as cationic or anionic, or neutral surfactants, such as non-ionic or zwitterionic. Neutral surfactants are preferred for personal care products and hygienic products that touch the skin of a user. Non-neutral surfactants may be chosen for non-skin contact use.

Suitable cationic surfactants can include pH-dependent primary, secondary, or tertiary amines, octenidine dihydrochloride, or permanently charged quaternary ammonium cations, such as, for example: 1) alkyltrimethylammonium salts including cetyl trimethylammonium bromide, hexadecyl trimethyl ammonium bromide, and cetyl trimethylammonium chloride, 2) cetylpyridinium chloride, 3) benzalkonium chloride, 4) benzethonium chloride, 5) 5-Bromo-5-nitro-1,3-dioxane, 6) dimethyldioctadecylammonium chloride, 7) cetrimonium bromide, 8) dioctadecyldimethylammonium bromide.

Suitable anionic surfactants may include: 1) those that contain anionic functional groups, such as sulfate, sulfonate, phosphate, and carboxylates, 2) prominent alkyl sulfates including ammonium lauryl sulfate, sodium lauryl sulfate, and the related alkyl-ether sulfates, 3) sodium laureth sulfate, also known as sodium lauryl ether sulfate, 4) sodium myreth sulfate, 5) docusates including dioctyl sodium sulfosuccinate, perfluorooctanesulfonate, perfluorobutanesulfonate, linear alkylbenzene sulfonates, 6) alkyl-aryl ether phosphates, and 7) alkyl ether phosphates. Carboxylates are also a suitable category of anionic surfactants and can include: 1) alkyl carboxylates, such as sodium stearate, 2) sodium lauroyl sarcosinate, and 3) carboxylate-based fluorosurfactants, such as perfluorononanoate or perfluorooctanoate.

Suitable non-ionic surfactants can include: 1) fatty alcohols, such as, cetyl alcohol, stearyl alcohol, and cetostearyl alcohol, and oleyl alcohol, 2) polyoxyethylene glycol alkyl ethers, 3) octaethylene glycol monododecyl ether, 4) pentaethylene glycol monododecyl ether, 5) polyoxypropylene glycol alkyl ethers, 6) glucoside alkyl ethers, 7) decyl glucoside, 8) lauryl glucoside, 9) octyl glucoside, 10) polyoxyethylene glycol octylphenol ethers, 11) Triton X-100, 12) polyoxyethylene glycol alkylphenol ethers, 13) Nonoxynol-9, 14) glycerol alkyl esters, such as glyceryl laurate, 15) polyoxyethylene glycol sorbitan alkyl esters, such as polysorbate, 16) sorbitan alkyl esters, such as spans, 17) cocamide MEA, 18) cocamide DEA, 19) dodecyldimethylamine oxide, 20) block copolymers of polyethylene glycol and polypropylene glycol, such as poloxamers, as for example, LUTROL® F127, and 21) polyethoxylated tallow amine (POEA).

Suitable zwitterionic surfactants can include: 1) sulfonates, such as in CHAPS (3-[(3-Cholamidopropyl)dimethylammonio]-1-propanesulfonate), 2) sultaines such as cocamidopropyl hydroxysultaine, 3) betaines, such as cocamidopropyl betaine, and 4) phosphates such as lecithin.

In a removing step, the organic solvent is removed from the odor control solution to form an odor control suspension. In one aspect, volatile and water miscible organic solvents are used during the dissolving step as a phase separation is formed with the HPIM during the mixing step, such that the odor control suspension can easily separate from the organic solvent allowing for removal of the organic solvent during the removing step. Other mechanisms may also be applied to drive off the organic solvent from the odor control suspension, such as, for example, those including heat, vacuum, or rotary evaporation. The odor control suspension can include a percent solids from about 0.1% to about 60%, about 5% to about 35%, or about 30%.

The odor control suspension may be applied to a substrate, such as, for example, a plurality of particles, a plurality of fibers, a film, a nonwoven, or combinations thereof. In an aspect, the substrate including the odor control suspension may be a liquid absorbent member. The method of applying the odor control suspension to the substrate can include coating, printing, spraying, dipping, soaking, and combinations thereof.

In another embodiment, 1 ml of PIM-1 and 80 microliters of an anthraquinone dye, solvent blue 59, were dissolved in tetrahydrofuran (10 mg/ml), both available from Sigma-Aldrich Corp, St. Louis, Mo., USA. The solution was stirred to mix until particles formed. The tetrahydrofuran was removed by rotary evaporation using ROTOVAPOR HEIDOLPH 2 model, available from Heidolph Instrument, Heidolph North America, Elk Grove Village, Ill., USA, to form an odor control suspension at 0.08% solids. Four 10.16 cm by 10.16 cm pieces of 1.18 gsm KIMWIPE wiper tissue webs were soaked in 5 ml of the odor control suspension. The four pieces were air dried at room temperature (22 degrees Celsius and 55 percent humidity) for 12 hours. The four pieces were further dried at 100 degrees Celsius for 4 hours. The wipes were green in color.

Referring to FIGS. 9A and 9B, in yet another embodiment, an odor-absorbing member 20 is included in a personal care product, such as for example, a diaper 200. The diaper 200 includes a chassis 202 formed by various components, including a barrier sheet 40, a topsheet 50, an odor-absorbing member 20, and an acquisition layer 36. Besides the above-mentioned components, the diaper 200 may also contain various other components as is known in the art, such as, for example, tissue wrap and distribution layer (not illustrated). Likewise, one or more of the layers referred to in FIG. 9B may also be eliminated in certain exemplary embodiments. The diaper 200 is shown as having an hourglass shape in an unfastened configuration in FIG. 9B. However, other shapes may be utilized, such as a generally rectangular shape, T-shape, or I-shape. In some embodiments, the diaper 200 may also include a pair of side panels, or ears, (not shown) that extend from the side edges 204 of the diaper 200 into one of the waist regions 206. The side panels may be integrally formed with a selected diaper component. For example, the side panels may be integrally formed with the barrier sheet 40.

The diaper 200 may also include a pair of containment flaps 208 that are configured to provide a barrier and to contain the lateral flow of body exudates. The containment flaps 208 may be located along the laterally opposed side edges 204 on an outwardly facing surface 218 of the topsheet 50 adjacent the side edges 204. The containment flaps 208 may extend longitudinally along the entire length of the diaper 200, or may only extend partially along the length of the diaper 200.

To provide improved fit and to help reduce leakage of body exudates, the diaper 200 may be elasticized with suitable elastic members. For example, the diaper 200 may include leg elastics 210 constructed to operably tension the side margins of the diaper 200 to provide elasticized leg bands which can closely fit around the legs of the wearer to reduce leakage and provide improved comfort and appearance. Waist elastics 212 may also be employed to elasticize the end margins 214 of the diaper 200 to provide elasticized waistbands. The waist elastics 212 are configured to provide a resilient, comfortably close fit around the waist of the wearer.

The diaper 200 may also include one or more fasteners 216. For example, two flexible fasteners 216 on opposite side edges 204 of waist regions 206 to create a waist opening and a pair of leg openings about the wearer. The shape of the fasteners 216 may generally vary, but may include, for instance, generally rectangular shapes, square shapes, circular shapes, triangular shapes, oval shapes, linear shapes, and so forth. The fasteners may include, for instance, a hook-and-loop material, buttons, pins, snaps, adhesive tape fasteners, cohesives, fabric-and-loop fasteners, etc. In one particular embodiment, each fastener 216 includes a separate piece of hook material affixed to the inside surface of a flexible backing.

The various regions and/or components of the diaper 200 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the barrier sheet 40 and topsheet 50 are assembled to each other and to the odor-absorbing member 20 using an adhesive. Similarly, other diaper 200 components, such as the leg elastic members 210, waist elastic members 212 and fasteners 216, may also be assembled into the diaper 200 using any attachment mechanism.

The odor-absorbing member 20 includes an odor control article 10 and a liquid absorbent member 30 that includes a web formed of cellulosic fibers and superabsorbent particles to absorb urine and fecal matter. The odor control article 10 is located between the laterally opposed side edges 204 and the longitudinally opposed end margins 214 in a central location of the liquid absorbent member 30. The odor control article 10 may be continuously coated on the liquid absorbent member 30 at the liquid absorbent member surface 31 that is adjacent to the acquisition layer 36. The odor control article 10 is made with a suspension of PIM-1 and an anthraquinone dye, solvent blue 35, available from Sigma-Aldrich Corp, St. Louis, Mo., USA, wherein the ratio of the colorant to PIM-1 can range from 0.001 to 0.15.

EXAMPLES

| Chemical Directory | |
|---|---|
| 3,3,3',3'-tetramethyl-1,1'-spirobisindane-5,5',6,6'-tetrol | TCI America, Portland OR, USA |
| Tetrafluoroterephthalonitrile | TCI America, Portland OR, USA |
| Dimethylformamide (DMF) | Sigma Aldrich, St. Louis, MO, USA |
| Potassium carbonate | Sigma Aldrich, St. Louis, MO, USA |
| Tetrahydrofuran (THF) | Sigma Aldrich, St. Louis, MO, USA |
| LUTROL ® F127 | BASF Corporation North America, Florham Park, NJ, USA |
| Undecanal | Sigma Aldrich, St. Louis, MO, USA |
| Solvent blue 59 | Sigma Aldrich, St. Louis, MO, USA |
| Oil of rosemary | Indofine Chemical Company, Inc., Hillsborough, NJ, USA |
| Lithium aluminum hydride | Sigma Aldrich, St. Louis, MO, USA |
| Dimethyl disulfide (DMDS) | Sigma Aldrich, St. Louis, MO, USA |
| 2,3-butanedione (BDO) | Sigma Aldrich, St. Louis, MO, USA |
| Triethylamine (TEA) | Sigma Aldrich, St. Louis, MO, USA |
| Butanal | Sigma Aldrich, St. Louis, MO, USA |
| Sodium bicarbonate | Sigma Aldrich, St. Louis, MO, USA |
| Copper (II) chloride tetrahydrate | Sigma Aldrich, St. Louis, MO, USA |

The following are various examples that illustrate aspects of the present disclosure:

Example Set 1

The qualitative testing of PIM-1 with neutral surfactant to treat garlic and undecanal odors was as follows:

1. Synthesis of PIM-1: 3.41 g of 3,3,3',3'-tetramethyl-1,1'-spirobisindane-5,5',6,6'-tetrol and 2 g of tetrafluoroterephthalonitrile were dissolved in 66 ml dimethylformamide (DMF). 2.76 g of potassium carbonate was added. Under stirring, the mixture was heated to 65 degrees Celsius for 72 hours. Upon cooling, the mixture was added to 400 ml water. The solid was filtered and was dried in an oven at 100 degrees Celsius for 2 hours. The solid was then dissolved in 50 ml tetrahydrofuran (THF) and dropped in to 500 ml water. The solid was collected and dried in an oven at 100 degrees Celsius for 2 hours. The compound was designated as PIM-1.

2. Preparation of PIM-1 with neutral surfactant particles and web coating: PIM-1 was dissolved in tetrahydrofuran. 2 ml of PIM-1 in tetrahydrofuran (40 mg/ml) was added dropwise into 50 ml of an aqueous solution of a 1% LUTROL® F127 neutral surfactant solution. The PIM-1 solution was stirred until particles formed. The tetrahydrofuran was removed by rotary evaporation using ROTOVAPOR HEIDOLPH 2 model to form an odor control suspension at 0.16% solids. Four 10.16 cm by 10.16 cm pieces of 0.86 g KIMWIPE wiper tissue webs were soaked in 5 ml of the odor control suspension. The four pieces were air dried at room temperature (22 degrees Celsius and 55 percent relative humidity) for two hours. The four pieces were further dried at 100 degrees Celsius for 5 hours.

3. Garlic odor absorption by PIM-1 with neutral surfactant particles on KIMWIPE wiper tissue webs: Two jars each contained three pieces of fresh garlic. A 10.16 cm by 10.16 cm piece of uncoated KIMWIPE wiper was placed in the first jar as a control sample. A piece of PIM-1 with neutral surfactant coated KIMWIPE wiper was placed in the second jar. The two jars were capped and allowed to sit at room temperature (22 degrees Celsius and 55 percent relative humidity) for two hours. A relatively strong garlic odor was detected when the first jar was opened, while relatively little garlic odor was detected upon opening of the second jar.

4. Undecanal odor absorption by PIM-1 with neutral surfactant particles on KIMWIPE wiper tissue webs: Two jars each contained saturated undecanal. Each jar was prepared by incubating a the jar with 0.2 ul undecanal liquid for 0.5 hours at 50 degrees Celsius, removing the jar from the incubator, and allowing the jar to reach room temperature (22 degrees Celsius and 55 percent relative humidity). A 10.16 cm by 10.16 cm piece of uncoated 0.86 g KIMWIPE wiper was placed in the first jar as a control sample. A piece of PIM-1 with neutral surfactant coated 0.86 g KIMWIPE wiper was placed in the second jar. The two jars were capped and allowed to sit at room temperature (22 degrees Celsius and 55 percent relative humidity) for two hours. A relatively strong undecanal odor was detected when the first jar was opened, while relatively little undecanal odor was detected upon opening of the second jar.

Example Set 2

The qualitative testing of PIM-1 with colorant to treat garlic and rosemary odors was as follows:

1. Preparation of PIM-1 with colorant on KIMWIPE wiper tissue webs: 1 ml of PIM-1 (available as described in the synthesis of PIM-1 in Example Set 1) and 80 microliters of solvent blue 59 were dissolved in tetrahydrofuran (10 mg/ml). The solution was stirred until particles formed. The tetrahydrofuran and some water were removed by rotary evaporation using ROTOVAPOR HEIDOLPH 2 model, to form an odor control suspension at 1% solids. Four 10.16 cm by 10.16 cm pieces of 0.86 g KIMWIPE wiper were soaked in 5 ml of the odor control suspension. The four pieces were air dried at room temperature (22 degrees Celsius and 55 percent humidity) for 2 hours. The four pieces were further dried at 100 degrees Celsius for 4 hours. The wipes were green in color.

2. Garlic odor absorption by PIM-1 with colorant on KIMWIPE wiper tissue webs: Two jars each contained three pieces of fresh garlic. A 10.16 cm by 10.16 cm piece of uncoated KIMWIPE wiper was placed in the first jar as a control sample. A piece of PIM-1 with colorant coated KIMWIPE wiper was placed in the second jar. The two jars were capped and allowed to sit at room temperature (22 degrees Celsius and 55 percent relative humidity) for one hour. A relatively strong garlic odor was detected when the first jar was opened, while relatively little garlic odor was detected upon opening the second jar.

3. Rosemary odor absorption by PIM-1 with colorant on KIMWIPE wiper tissue webs: Two jars each contained saturated rosemary. Each jar was prepared by incubating the jar with 0.1 ml oil of rosemary for one hour at 50 degrees Celsius, removing the jar from the incubator, and allowing the jar to reach room temperature (22 degrees Celsius and 55 percent relative humidity). A 10.16 cm by 10.16 cm piece of uncoated 0.86 g KIMWIPE wiper was placed in the first jar as a control sample. A piece of PIM-1 with colorant coated 0.86 g KIMWIPE wiper was placed in the second jar. The two jars were capped and allowed to sit at room temperature (22 degrees Celsius and 55 percent relative humidity) for one hour. A relatively strong rosemary odor was detected when the first jar was opened, while relatively little rosemary odor was detected upon opening the second jar.

Example Set 3

The qualitative testing of PIM-2 to treat garlic odors was as follows:

1. Synthesis of PIM-2: 2 g of PIM-1 were dissolved in 100 ml of tetrahydrofuan (THF) solution and the solution was cooled in an ice bath under stirring. 0.5 g of lithium aluminum hydride was then added. The ice bath was then removed and the mixture was warmed up to room temperature for 20 minutes. Under stirring, the mixture was then heated to 65 degrees Celsius for 72 hours. Upon cooling, the mixture was added to 400 ml water. The solid was filtered and was dried in an oven at 100 degrees Celsius for 2 hours. The solid was then dissolved in 50 ml THF and dropped in to 500 ml water. The solid was collected and dried in an oven at 100 degrees Celsius for 2 hours. The compound was designated as PIM-2.

2. Coating of PIM-2 on KIMWIPE wiper tissue webs: 118 mg of PIM-2 were dissolved in 50 ml of tetrahydrofuran forming a PIM-2 mixture. A 10.16 cm by 10.16 cm piece of 0.86 g KIMWIPE wiper tissue web was soaked with the PIM-2 mixture. The web was air-dried at room temperature (22 degrees Celsius and 55 percent relative humidity) and then dried at 100 degrees Celsius for 5 hours.

3. Garlic odor absorption by PIM-2 particles on KIMWIPE wiper tissue webs: Two jars each contained three pieces of fresh garlic. A 10.16 cm by 10.16 cm piece of uncoated KIMWIPE wiper was placed in the first jar as a control sample. A piece of PIM-2 coated KIMWIPE wiper was placed in the second jar. The two jars were capped and allowed to sit at room temperature (22 degrees Celsius and 55 percent relative humidity) for five minutes. A relatively strong garlic odor was detected when the first jar was opened, while relatively little garlic odor was detected upon opening of the second jar.

Example Set 4

The quantitative testing of PIM-1 to treat dimethyl disulfide, butanedione, triethylamine, and butanal odors was as follows:

1. Preparation and coating of PIM-1 on KIMWIPE wiper tissue webs: 300 mg of PIM-1 (available as described in the synthesis of PIM-1 in Example Set 1) was dissolved in 100 ml of tetrahydrofuran forming a PIM-1 mixture. Thirty 10.16 cm by 10.16 cm pieces of 0.86 g KIMWIPE wiper tissue webs were soaked with the PIM-1 mixture. The webs were air-dried at room temperature (22 degrees Celsius and 55 percent relative humidity) for 12 hours and then dried at 100 degrees Celsius for 5 hours.

2. Odor absorption of dimethyl disulfide (DMDS) by PIM-1 on KIMWIPE wiper tissue webs: Ten vials were designated as Sample 1 through 10. Sample 1 vial contained 7 microliters of DMDS. Sample 2 and sample 10 vials each contained 7 microliters of DMDS and one 10.16 cm by 10.16 cm piece of uncoated 0.86 g KIMWIPE wiper. Sample 3, 4, 5, 6, 7, 8, and 9 vials each contained a piece of PIM-1 coated 0.86 g KIMWIPE wiper (10 mg PIM-1 per KIMWIPE wiper) and 1, 2, 3, 4, 5, 6, and 7 microliters of DMDS, respectively. The samples were incubated at 38 degrees Celsius for 60 minutes prior to gas chromatography (GC) analysis. The GC results for DMDS absorption are shown in Table 1.

TABLE 1

| Sample | KIMWIPE Treatment | PIM-1 Amount (mg) | DMDS added (micro-liter) | GC Peak | Total amount of DMDS absorbed (mg) | Total amount of DMDS absorbed (%) |
|---|---|---|---|---|---|---|
| 1 | No KIMWIPE | None | 7.42 | 2709 | | |
| 2 | Uncoated | None | 7.42 | 2247 | | |
| 3 | PIM-1 | 10 | 1.06 | 53 | 0.91 | 86 |
| 4 | PIM-1 | 10 | 2.12 | 245 | 1.45 | 68 |
| 5 | PIM-1 | 10 | 3.18 | 368 | 2.17 | 68 |
| 6 | PIM-1 | 10 | 4.25 | 769 | 2.13 | 50 |
| 7 | PIM-1 | 10 | 5.30 | 827 | 3.03 | 57 |
| 8 | PIM-1 | 10 | 6.36 | 1213 | 3.03 | 48 |

TABLE 1-continued

| Sample | KIMWIPE Treatment | PIM-1 Amount (mg) | DMDS added (microliter) | GC Peak | Total amount of DMDS absorbed (mg) | Total amount of DMDS absorbed (%) |
|---|---|---|---|---|---|---|
| 9 | PIM-1 | 10 | 7.42 | 1496 | 3.32 | 45 |
| 10 | Uncoated | None | 7.42 | 2196 | | |

3. Odor absorption of 2,3-butanedione (BDO) by PIM-1 on KIMWIPE wiper tissue webs-Data Set 1: Nine vials were designated as Sample 1 through 9. Sample 1 vial contained 7 microliters of BDO. Sample 2 vial contained 7 microliters of BDO and one 10.16 cm by 10.16 cm piece of uncoated 0.86 g KIMWIPE wiper. Sample 3, 4, 5, 6, 7, 8, and 9 vials each contained a piece of PIM-1 coated 0.86 g KIMWIPE wiper (10 mg PIM-1 per KIMWIPE wiper) and 1, 2, 3, 4, 5, 6, and 7 microliters of BDO, respectively. The samples were incubated at 38 degrees Celsius for 60 minutes prior to gas chromatography (GC) analysis. The GC results for BDO absorption Data Set 1 are shown in Table 2.

TABLE 2

| Sample | KIMWIPE Treatment | PIM-1 Amount (mg) | BDO added (microliter) | GC Peak | Total amount of BDO absorbed (mg) | Total amount of BDO absorbed (%) |
|---|---|---|---|---|---|---|
| 1 | No KIMWIPE | None | 6.67 | 1113 | | |
| 2 | Uncoated | None | 6.67 | 944 | | |
| 3 | PIM-1 | 10 | 0.98 | 29 | 0.81 | 83 |
| 4 | PIM-1 | 10 | 1.96 | 80 | 1.49 | 76 |
| 5 | PIM-1 | 10 | 2.94 | 77 | 2.50 | 85 |
| 6 | PIM-1 | 10 | 3.92 | 278 | 2.27 | 58 |
| 7 | PIM-1 | 10 | 4.91 | 299 | 3.14 | 64 |
| 8 | PIM-1 | 10 | 5.89 | 351 | 3.83 | 65 |
| 9 | PIM-1 | 10 | 6.67 | 434 | 4.20 | 63 |

4. Odor absorption of triethylamine (TEA) by PIM-1 on KIMWIPE wiper tissue webs: Fifteen vials were designated as Sample 1 through 15. Sample 1, 2, and 3 vials each contained 1 microliter of TEA. Sample 4 vial contained 7 microliters of TEA and one 10.16 cm by 10.16 cm piece of uncoated 0.86 g KIMWIPE wiper. Sample 5 through 15 vials each contained a piece of PIM-1 coated 0.86 g KIMWIPE wiper (10 mg PIM-1 per KIMWIPE wiper) and 1, 2, 3, 4, 5, 6, 7, 7, and 7 microliters of TEA, respectively. The samples were incubated at 38 degrees Celsius for 60 minutes prior to gas chromatography (GC) analysis. The GC results for TEA absorption are shown in Table 3.

TABLE 3

| Sample | KIMWIPE Treatment | PIM-1 Amount (mg) | TEA added (microliter) | GC Peak | Total amount of TEA absorbed (mg) | Total amount of TEA absorbed (%) |
|---|---|---|---|---|---|---|
| 1 | No KIMWIPE | None | 0.73 | 321 | | |
| 2 | No KIMWIPE | None | 2.19 | 951 | | |
| 3 | No KIMWIPE | None | 5.11 | 2213 | | |
| 4 | PIM-1 | None | 5.11 | 2030 | | |
| 5 | PIM-1 | 10 | 0.73 | 121 | 0.42 | 60 |
| 6 | PIM-1 | 10 | 1.46 | 256 | 0.81 | 55 |
| 7 | PIM-1 | 10 | 2.19 | 393 | 1.19 | 54 |
| 8 | PIM-1 | 10 | 2.92 | 549 | 1.52 | 52 |
| 9 | PIM-1 | 10 | 3.65 | 890 | 1.39 | 38 |
| 10 | PIM-1 | 10 | 4.38 | 879 | 2.15 | 49 |
| 11 | PIM-1 | 10 | 5.11 | 1409 | 1.54 | 30 |
| 12 | PIM-1 | 10 | 5.11 | 1524 | 1.25 | 24 |
| 13 | PIM-1 | 10 | 5.11 | 1403 | 1.56 | 30 |
| 14 | Uncoated | None | 5.11 | 2030 | | |
| 15 | Uncoated | None | 5.11 | 2008 | | |

5. Odor absorption of butanal by PIM-1 on KIMWIPE wiper tissue webs: Eighteen vials were designated as Sample 1 through 18. Each of Sample 1 through 7 vials each contained one 10.16 cm by 10.16 cm piece of uncoated 0.86 g KIMWIPE wiper and a different amount of butanal from 7, 5, 3, 1, 4, 4, and 0 microliters of butanal. Sample 8 through 16 vials each contained a piece of PIM-1 coated 0.86 g KIMWIPE wiper (10 mg PIM-1 per KIMWIPE wiper) and 1, 2, 3, 4, 5, 6, 7, 7, and 7 microliters of butanal, respectively. Sample 17 and 18 each contained one 10.16 cm by 10.16 cm piece of uncoated 0.86 g KIMWIPE wiper and 4 microliters of butanal. The samples were incubated at 38 degrees Celsius for 60 minutes prior to gas chromatography (GC) analysis. The GC results for butanal absorption are shown in Table 4.

TABLE 4

| Sample | KIMWIPE Treatment | PIM-1 Amount (mg) | Butanal added (microliter) | GC Peak | Total amount of Butanal absorbed (mg) | Total amount of Butanal absorbed (%) |
| --- | --- | --- | --- | --- | --- | --- |
| 1 | Uncoated | None | 5.6 | 1602 | | |
| 2 | Uncoated | None | 4 | 800 | | |
| 3 | Uncoated | None | 2.4 | 489 | | |
| 4 | Uncoated | None | 0.8 | 166 | | |
| 5 | Uncoated | None | 3.2 | 617 | | |
| 6 | Uncoated | None | 3.2 | 648 | | |
| 7 | Uncoated | None | 0.0 | None | | |
| 8 | PIM-1 | 10 | 0.8 | 31 | 0.58 | 73 |
| 9 | PIM-1 | 10 | 1.6 | 81 | 1.06 | 66 |
| 10 | PIM-1 | 10 | 2.4 | 153 | 1.45 | 60 |
| 11 | PIM-1 | 10 | 3.2 | 230 | 1.8 | 60 |
| 12 | PIM-1 | 10 | 4.0 | 222 | 2.57 | 64 |
| 13 | PIM-1 | 10 | 4.8 | 312 | 2.87 | 60 |
| 14 | PIM-1 | 10 | 5.6 | 389 | 3.23 | 58 |
| 15 | PIM-1 | 10 | 5.6 | 420 | 3.07 | 55 |
| 16 | PIM-1 | 10 | 5.6 | 685 | 1.81 | 32 |
| 17 | Uncoated | None | 3.2 | 530 | | |
| 18 | Uncoated | None | 3.2 | 640 | | |

6. Odor absorption of 2,3-butanedione (BDO) by PIM-1 on KIMWIPE wiper tissue webs-Data Set 2: Fifteen vials were designated as Sample 1 through 15. Each of Sample 1 through 5 vials each contained a one 10.16 cm by 10.16 cm piece of PIM-1 coated 0.86 g KIMWIPE wiper (10 mg PIM-1 per KIMWIPE wiper) and 4, 6, 8, 10, and 12 microliters of BDO, respectively. Sample 6 through 15 vials each contained only BDO in the amount of 2, 4, 6, 8, 10, 12, 12, 12, 12, and 12 microliters, respectively. The samples were incubated at 38 degrees Celsius for 60 minutes prior to gas chromatography (GC) analysis. The GC results for BDO absorption Data Set 2 are shown in Table 5.

TABLE 5

| Sample | KIMWIPE Treatment | PIM-1 Amount (mg) | BDO added (microliter) | GC Peak | Total amount of BDO absorbed (mg) | Total amount of BDO absorbed (%) |
| --- | --- | --- | --- | --- | --- | --- |
| 1 | PIM-1 | 10 | 3.92 | 167 | 3.0 | 76 |
| 2 | PIM-1 | 10 | 5.88 | 361 | 3.6 | 62 |
| 3 | PIM-1 | 10 | 7.84 | 463 | 4.6 | 58 |
| 4 | PIM-1 | 10 | 9.80 | 703 | 4.5 | 46 |
| 5 | PIM-1 | 10 | 11.76 | 896 | 4.6 | 39 |
| 6 | None | None | 1.96 | 367 | | |
| 7 | None | None | 3.92 | 684 | | |
| 8 | None | None | 5.88 | 939 | | |
| 9 | None | None | 7.84 | 1110 | | |
| 10 | None | None | 9.80 | 1297 | | |
| 11 | None | None | 11.76 | 1416 | | |
| 12 | None | None | 11.76 | 1781 | | |
| 13 | None | None | 11.76 | 1532 | | |
| 14 | None | None | 11.76 | 1444 | | |
| 15 | None | None | 11.76 | 1511 | | |

Example Set 5

The quantitative testing of copper ion-coated nanoparticles immobilized by PIM-1 to treat 2,3-butanedione (BDO) was as follows:

1. Coating of PIM-1 and copper ion-coated nanoparticles on KIMWIPE wiper tissue webs: Twenty-four vials were designated as Sample 1 through 24.

Sample 1, 9 and 17 vials each contained nothing.
Sample 2, 10 and 18 vials each contained 10 mg of copper ion-coated nanoparticles.
Sample 3, 11, and 19 vials each contained 1.0 mg of PIM-1.
Sample 4, 12 and 20 vials each contained 0.1 mg PIM-1.
Sample 5, 13 and 21 vials each contained 2.0 mg PIM-1.
Sample 6, 14 and 22 vials each contained 10.0 mg copper ion-coated nanoparticles coated with 1.0 mg PIM-1.
Sample 7, 15 and 23 vials each contained 10.0 mg copper ion-coated nanoparticles coated with 0.1 mg PIM-1.
Sample 8, 16 and 24 vials each contained 10.0 mg copper ion-coated nanoparticles with 2.0 mg PIM-1.

For vials containing only the PIM-1 coating, that is, Sample 3, 4, 5, 11, 12, 13, 19, 20, and 21 vials, the appropriate amount of PIM-1 (available as described in the synthesis of PIM-1 in Example Set 1), by weight, was dissolved in 50 ml of tetrahydrofuran (THF) forming a PIM-1 mixture.

For vials containing only the copper ion-coated nanoparticle coating, that is, Sample 2, 10 and 18 vials, a solution of silica nanoparticles of approximately 25 nanometers, obtained under the commercial name SNOWTEX OXS (available from Nissan Chemical America Corporation, Houston, Tex., USA) was prepared (25 ml stock and 100 ml of water, 5.26 g $SiO_2$, 8.47 micromole particle $SiO_2$). Sodium bicarbonate was prepared in aqueous solution (350 ml, 0.05 M final concentration for 500 ml) and was added to the SNOWTEX, silica stock solution. Copper (II) chloride tetrahydrate was prepared in aqueous solution (1.14 g, 8.47 micromole in 40 ml water). The copper solution was added to the SNOWTEX-sodium bicarbonate solution with vigorous stirring for 2 hours at room temperature (22 degrees Celsius and 55 percent relative humidity). The liquid was removed from the resulting solution in vacuo, the isolated solid was washed with several portions of distilled water and allowed to air dry at room temperature to provide dry copper ion-coated nanoparticles. The dry copper ion-coated nanoparticles had approximately a 50:1 metal ion to silica particle mole ratio. A suspension of the copper ion-coated nanoparticles in THF was prepared by adding 50 ml of THF to the appropriate amount of copper ion-coated nanoparticles as specified for each sample, by weight.

For vials containing the copper ion-coated nanoparticle and PIM-1 coating, that is, Sample 6, 7, 8, 14, 15, 16, 22, 23, and 24, copper ion-coated nanoparticles were synthesized by the method described for vials containing only the copper ion-coated nanoparticles (Sample 2, 10 and 18). The dry copper ion-coated nanoparticles were then added to the appropriate amount of PIM-1 for the given sample. A suspension of the copper ion-coated nanoparticles and PIM-1 was prepared by adding 50 ml of THF to the given sample.

Twenty-four 10.16 cm by 10.16 cm pieces of 0.86 g KIMWIPE wiper tissue webs were each coated with the coatings described above by taking the webs and dipping them into each solution to saturation. The webs were then hung in a fume hood and were air-dried at room temperature (22 degrees Celsius and 55 percent relative humidity) for 12 hours and then dried at 100 degrees Celsius for 5 hours.

2. Odor absorption of 2,3-butanedione by PIM-1 and copper ion-coated nanoparticles on KIMWIPE wiper tissue webs: Each KIMWIPE wiper tissue web was placed in a 20 ml headspace vial and designated as Sample 1 through 24, to correspond respectively with the coating sample vial number as described in Step 1. Each vial contained 5 microliters of 2,3-butanedione (BDO). Six 20 ml headspace vials were prepared and each vial only contained 5 microliters of BDO; the vials were designated as samples 25, 26, 27, 28, 29 and 30. The samples were incubated at 38 degrees Celsius for 60 minutes prior to gas chromatography (GC) analysis. The GC results for BDO absorption are shown in Table 6.

TABLE 6

| Sample | KIMWIPE Treatment | PIM-1 Amount (mg) | Copper Amount (mg) | BDO added (microliter) | GC Peak | Total amount of BDO absorbed (mg) | Total amount of BDO absorbed (%) |
|---|---|---|---|---|---|---|---|
| 1 | None | 0 | 0 | 5 | 794 | 0.1 | 1.3 |
| 2 | Copper | 0 | 10 | 5 | 505 | 1.8 | 37.3 |
| 3 | PIM-1 | 1 | 0 | 5 | 719 | 0.5 | 10.7 |
| 4 | PIM-1 | 0.1 | 0 | 5 | 824 | −0.1 | −2.4 |
| 5 | PIM-1 | 2 | 0 | 5 | 651 | 0.9 | 19.1 |
| 6 | Copper and PIM-1 | 1 | 10 | 5 | 427 | 2.3 | 47.0 |
| 7 | Copper and PIM-1 | 0.1 | 10 | 5 | 475 | 2.0 | 41.0 |
| 8 | Copper and PIM-1 | 2 | 10 | 5 | 451 | 2.2 | 43.9 |
| 9 | None | 0 | 0 | 5 | 777 | 0.2 | 3.5 |
| 10 | Copper | 0 | 10 | 5 | 540 | 1.6 | 32.9 |
| 11 | PIM-1 | 1 | 0 | 5 | 715 | 0.6 | 11.2 |
| 12 | PIM-1 | 0.1 | 0 | 5 | 814 | −0.1 | −1.1 |
| 13 | PIM-1 | 2 | 0 | 5 | 648 | 1.0 | 19.5 |
| 14 | Copper and PIM-1 | 1 | 10 | 5 | 495 | 1.9 | 38.5 |
| 15 | Copper and PIM-1 | 0.1 | 10 | 5 | 513 | 1.8 | 36.3 |
| 16 | Copper and PIM-1 | 2 | 10 | 5 | 384 | 2.6 | 52.3 |

TABLE 6-continued

| Sample | KIMWIPE Treatment | PIM-1 Amount (mg) | Copper Amount (mg) | BDO added (microliter) | GC Peak | Total amount of BDO absorbed (mg) | Total amount of BDO absorbed (%) |
|---|---|---|---|---|---|---|---|
| 17 | None | 0 | 0 | 5 | 746 | 0.4 | 7.3 |
| 18 | Copper | 0 | 10 | 5 | 549 | 1.6 | 31.8 |
| 19 | PIM-1 | 1 | 0 | 5 | 709 | 0.6 | 11.9 |
| 20 | PIM-1 | 0.1 | 0 | 5 | 796 | 0.1 | 1.1 |
| 21 | PIM-1 | 2 | 0 | 5 | 665 | 0.9 | 17.4 |
| 22 | Copper and PIM-1 | 1 | 10 | 5 | 481 | 2.0 | 40.3 |
| 23 | Copper and PIM-1 | 0.1 | 10 | 5 | 538 | 1.6 | 33.1 |
| 24 | Copper and PIM-1 | 2 | 10 | 5 | 434 | 2.3 | 46.1 |
| 25 | No KIMWIPE | 0 | 0 | 5 | 842 | | |
| 26 | No KIMWIPE | 0 | 0 | 5 | 807 | | |
| 27 | No KIMWIPE | 0 | 0 | 5 | 794 | | |
| 28 | No KIMWIPE | 0 | 0 | 5 | 787 | | |
| 29 | No KIMWIPE | 0 | 0 | 5 | 814 | | |
| 30 | No KIMWIPE | 0 | 0 | 5 | 786 | | |

Gas Chromatography Test Method

The gas chromatography procedure for testing odor absorption was as follows:

1. KIMWIPE wiper samples were added to the vials as specified in the examples.

2. The specified amount of odorant (2,3-butanedione, triethylamine, butanal, or dimethyl disulfide) in microliter quantities was added to a 20 ml headspace vial (flat bottom headspace crimp top glass vials, 20 ml 25×75 mm, available from Agilent Technologies, Santa Clara, Calif., USA). The odorant was added to the side of the vial near the top such that the liquid odorant was not added directly onto the KIMWIPE wiper. A TEFLON-faced septa closure was placed on the top of the vial to prevent the escape of any vapor. The vial was positioned at an angle such that the vial was nearly horizontal and rotated such that the liquid was distributed near the top of the vial.

3. The closure was crimped to seal the vial.

4. The sample vials were incubated at 38 degrees Celsius for 60 minutes. Refer to the headspace parameters of TABLE 7 for the oven settings.

5. The vials were then tested by removing an aliquot of headspace and injecting it into the gas chromatograph (GC) with a Thermal Conductivity Detector (Agilent 6890 GC, Agilent Technologies, Santa Clara, Calif., USA) using a headspace analyzer (Agilent 7694 HSA, Agilent Technologies, Santa Clara, Calif., USA). The separation column is a RESTEK RTX-Volatile Amine column, available from Restek Corporation, Bellefonte, Pa., USA. The control, a vial containing a clean KIMWIPE wiper, was tested to define 0% odor removal. The peak area for the particular odorous gas obtained from the sample is compared to the peak area from the control.

6. Data handling: The data from the GC is collected and processed using the Agilent Technologies GC CHEMSTATION software (Rev. A.10.01 [1635]), available from Agilent Technologies, Santa Clara, Calif., USA. The data is stored on the GC computer where the CHEMSTATION software resides and backed up on another computer.

TABLE 7

| | |
|---|---|
| Chromatograph | Agilent Technologies 6890 with Agilent Technologies 7694 Headspace Sampler |
| Column | RESTEK RTX-VolatileAmine (30 m, 0.32 mm ID) catalog # 18077, S/N 1021659, |
| GC Oven Program | |
| BDO | 110° C., isothermal time 5.5 minutes |
| TEA | 150° C., isothermal time 5 minutes |
| DMDS | 180° C., isothermal time 5 minutes |
| Butanal | 110° C., isothermal time 4.5 minutes |
| Carrier Gas | Varies, He at 9-12 psi (1.2 to 1.7 ml/min.) |
| Headspace Aux | 15.0 psi |
| Injector | Split flow = 15-25 ml/min |
| Temperature | 125-175° C. |
| Detector | Thermal Conductivity @ 150-250° C. |
| Retention time | |
| TEA | 4.6 minutes |
| DMDS | 3.6 minutes |
| Butanal | 3.7 minutes |
| BDO | 4.2 minutes |

TABLE 7-continued

Agilent 7694 Headspace

| | |
|---|---|
| Oven | 38° C. |
| Loop | 85° C. |
| Transfer line | 110° C. |
| Vial Equilibrium Time | 60 minutes |
| Press. Time | 0.20 minutes |
| Loop Fill | 0.20 minutes |
| Loop Equilibrium Time | 0.15 minutes |
| Injection Time | 0.30 minutes |
| GC Cycle Time | Varies, 4.5 to 5.5 minutes |

Gel Permeation Chromatography (GPC) Test Method

The gas chromatography procedure for measuring the molar mass distribution of the HPIM was as follows:

1. Approximately 10 mg of the PIM-1 polymer was accurately weighed in replicate into two 20 ml scintillation vials (Wheaton Scientific Products No. 986568, available from Wheaton Science Products, Millville, N.J., USA) and covered with 10.0 ml of stabilized tetrahydrofuran (THF) at room temperature (22 degrees Celsius and 55 percent humidity).

2. The vials were covered with aluminum foil and screwed closed with the vial cap at room temperature.

3. The samples were placed on the PL-SP 260 Prep Station (Agilent Technologies, Santa Clara, Calif., USA) and shaken overnight at room temperature.

4. The following day the samples were filtered through a 0.45 micron Whatman 25 mm GD/X PTFE filter into 2 ml autosampler vials (NATIONAL SCIENTIFIC C5000-186W, available National Scientific Company, Rockwood, Tenn., USA) from and made GPC ready. The GPC conditions are in TABLE 8.

TABLE 8

| | |
|---|---|
| System | Agilent Series 1100 HPLC (Agilent Technologies, Santa Clara, CA, USA) |
| Columns | (2) 10 micron PLgel MIXED-BLS 300 × 7.5 mm (part #PL1110-6100LS), (Agilent Technologies, Santa Clara, CA, USA) |
| Column Temperature | 35° C. |
| Eluent | THF (stabilized) |
| Flow rate | 1.0 ml/min |
| Injection | 100 µl |
| Detector | Agilent Series 1100 Refractive Index at 35° C. (Agilent Technologies, Santa Clara, CA, USA) |
| Software | CHEMSTATION Rev B.04.03 with GPC Data Analysis Software Rev. B.01.01, (Agilent Technologies, Santa Clara, CA, USA) |

5. Calibration Curve Generation: Three vials of EAS-IVIAL PS-H (2 ml) polystyrene standards (PS) (part #PL2010-0201, available from Agilent Technologies, Santa Clara, Calif., USA)), representing a molar mass range from 162 to 6,035,000 Da, were solubilized in 2.0 ml of THF on the day of analysis at room temperature.

6. Standards were placed on the PL-SP 260 Prep Station and shaken for one hour to effect solution at room temperature.

7. An eleven point calibration curve with a 3rd order fit was generated with the PS standard calibration data shown in TABLE 9. The highest molar mass PS was excluded from this curve.

TABLE 9

| Sample No. | Volume (ml) | Molar Mass (Dalton) | Stat. Weight | Sample Name | Slope | Deviation (%) |
|---|---|---|---|---|---|---|
| 1 | 10.9152 | 3053000.00 | 1.00 | PS Mix 3 (y) | −0.5060 | −2.0864 |
| 2 | 11.8798 | 915000.00 | 1.00 | PS Mix 1 (g) | −0.5117 | 5.4068 |
| 3 | 12.4918 | 483000.00 | 1.00 | PS Mix 2 (r) | −0.5156 | −3.1688 |
| 4 | 13.2695 | 184900.00 | 1.00 | PS Mix 3 (y) | −0.5208 | 0.0103 |
| 5 | 14.1695 | 60450.00 | 1.00 | PS Mix 1 (g) | −0.5273 | 3.2734 |
| 6 | 15.1127 | 19720.00 | 1.00 | PS Mix 2 (r) | −0.5345 | −0.0434 |
| 7 | 15.8472 | 8450.00 | 1.00 | PS Mix 3 (y) | −0.5405 | −6.0046 |
| 8 | 16.5455 | 3370.00 | 1.00 | PS Mix 1 (g) | −0.5464 | −1.6310 |
| 9 | 17.3158 | 1260.00 | 1.00 | PS Mix 2 (r) | −0.5533 | −0.7823 |
| 10 | 17.8415 | 580.00 | 1.00 | PS Mix 3 (y) | −0.5581 | 10.0088 |
| 11 | 18.9287 | 162.00 | 1.00 | PS Mix 1 (g) | −0.5687 | −3.8631 |

8. PIM-1 molar mass distributions (MMD) were calculated based on the curve generated in Step 7 and were as follows in TABLE 10 and TABLE 11:

TABLE 10

PIM-1 MMD Data Set #1

| | |
|---|---|
| Mn (g/mol): | 30.4 kDa |
| Mw (g/mol): | 177.2 kDa |
| Mz (g/mol): | 360.8 kDa |
| D (Mw/Mn): | 5.83 |

TABLE 11

PIM-1 MMD Data Set #2

| | |
|---|---|
| Mn (g/mol): | 32.0 kDa |
| Mw (g/mol): | 159.0 kDa |
| Mz (g/mol): | 257.3 kDa |
| D (Mw/Mn): | 4.98 |

When introducing elements of the present disclosure or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the invention

What is claimed is:

1. An odor control article comprising:
   a hydrophobic polymer of intrinsic microporosity configured to absorb an odorous compound selected from the group consisting of volatile aldehydes, volatile ketones, volatile fatty acids, volatile amine derivatives, volatile sulfur derivatives, volatile thiol derivatives, and combinations thereof; and
   a colorant wherein a ratio of the colorant to the hydrophobic polymer of intrinsic microporosity by weight is from 0.001 to 0.3.

2. The odor control article of claim 1 wherein the hydrophobic polymer of intrinsic microporosity weight average molecular weight, $M_w$, is in the range from 1 kDa to 177 kDa.

3. The odor control article of claim 1 wherein the hydrophobic polymer of intrinsic microporosity is in the form of a plurality of particles, a plurality of fibers, or combinations thereof.

4. The odor control article of claim 1 wherein the hydrophobic polymer of intrinsic microporosity is repeating units of the formula, PIM-1:

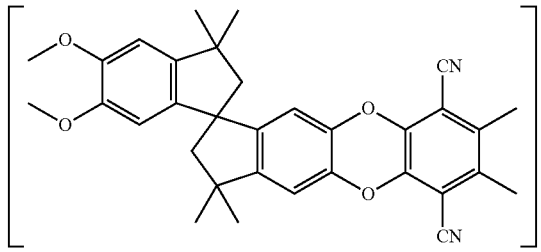

which may be substituted or unsubstituted.

5. The odor control article of claim 1 wherein the hydrophobic polymer of intrinsic microporosity has an odor absorption capacity for the odorous compound of about 86% by weight after a 5 minute exposure time.

6. The odor control article of claim 1 further comprising an active selected from the group consisting of an antimicrobial agent, an enzyme inhibitor, a fragrance, a plurality of metal ion-coated nanoparticles, and a combination thereof.

7. An odor-absorbing member comprising:
   a substrate having a surface, the substrate selected from the group consisting of a plurality of particles, a plurality of fibers, a film, a nonwoven web, and combinations thereof; and
   an odor control article comprising a hydrophobic polymer of intrinsic microporosity and a colorant;
   wherein a ratio of the colorant to the hydrophobic polymer of intrinsic microporosity by weight is from 0.001 to 0.3 and wherein the odor control article is disposed on the substrate surface and/or within the substrate.

8. The odor-absorbing member of claim 7 wherein the hydrophobic polymer of intrinsic microporosity is configured to absorb an odorous compound selected from the group consisting of volatile aldehydes, volatile ketones, volatile fatty acids, volatile amine derivatives, thiol derivatives and combinations thereof.

9. The odor-absorbing member of claim 7 wherein the odor control article is disposed as a coating on the substrate surface.

10. The odor-absorbing member of claim 9 wherein the coating is continuous.

11. The odor-absorbing member of claim 7 wherein the substrate is a liquid absorbent member.

12. The odor-absorbing member of claim 7 further comprising a barrier sheet adjacent to the substrate.

13. A liquid absorbent article comprising:
    a topsheet;
    a barrier sheet; and
    a liquid absorbent member positioned between the topsheet and the barrier sheet; and
    the odor-absorbing member of claim 7 disposed between the topsheet and the barrier sheet.

14. A liquid absorbent article comprising:
    a topsheet;
    a barrier sheet; and
    a liquid absorbent member positioned between the topsheet and the barrier sheet; and
    the odor-absorbing member of claim 7 disposed between the topsheet and the liquid absorbent member.

15. A liquid absorbent article comprising:
    a topsheet;
    a barrier sheet; and
    a liquid absorbent member positioned between the topsheet and the barrier sheet; and
    the odor-absorbing member of claim 7 disposed between the barrier sheet and the liquid absorbent member.

* * * * *